United States Patent
Al-Kaysi

(10) Patent No.: US 10,259,941 B1
(45) Date of Patent: Apr. 16, 2019

(54) MICROCRYSTAL EXFOLIATION BY UV LIGHT IRRADIATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Rabih O. Al-Kaysi, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 16/180,124

(22) Filed: Nov. 5, 2018

Related U.S. Application Data

(63) Continuation of application No. 15/947,426, filed on Apr. 6, 2018.

(51) Int. Cl.
  *C09B 1/02*     (2006.01)
  *C07C 68/08*    (2006.01)
  *A61L 15/62*    (2006.01)

(52) U.S. Cl.
  CPC ............... *C09B 1/02* (2013.01); *C07C 68/08* (2013.01); *A61L 15/62* (2013.01); *C07B 2200/13* (2013.01)

(58) Field of Classification Search
  None
  See application file for complete search history.

(56) References Cited

FOREIGN PATENT DOCUMENTS

| CN | 105199282 A | 12/2015 |
|---|---|---|
| GB | 438960 | 11/1935 |

OTHER PUBLICATIONS

Kim et al, Angewandte Chemie International Edition, Photoinduced Curling of Organic Molecular Crystal Nanowires, 2013, 52, pp. 6889-6893 and supplementary info. pp. 1-17. (Year: 2013).*

Lingyan Zhu, et al., "Crystal Structures and Photophysical Properties of 9-Anthracene Carboxylic Acid Derivatives for Photomechanical Application," Crystal Growth & Design, vol. 11, Sep. 6, 2011, pp. 4975-4983.

Lingyan Zhu, et al., "Improved Solid-State Photomechanical Materials by Fluorine Substitution of 9-Anthracene Carboxylic Acid", Chemistry of Materials, vol. 26, No. 20, Sep. 15, 2014, pp. 6007-6015.

Lingyan Zhu, et al., "Characterization of a P-type photomechanical molecular crystal based on the E →Z photoisomerization of 9-divinylanthracene malonitrile", Journal of Materials Chemistry C, vol. 4, Issue 35, Aug. 10, 2016, pp. 8245-8252.

Rabih O. Al-Kaysi, et al., "Chemical reaction method for growing photomechanical organic microcrystals", CrystEngComm, vol. 17, Issue 46, Jan. 7, 2015, pp. 8835-8842.

Rabih O. Al-Kaysi, et al., "Photo-Induced Spontaneous Coiling and Bending of Molecular-Crystal Nanowires, Microrods and Micro-Multipods", Conference: ICNFA '13, at Toronto, Canada, Aug. 2013, pp. 1-3.

Zaragoza Dorwald, Side Reactions in Organic Synthesis, 2005, WILEY-VCH Verlag GmbH & Co. KGaA, Weinheim, Preface. p. IX. (Year: 2005).

Pajula et al (Molecular Pharmaceutics, Predicting the Formation and Stability of Amorphous Small Molecule Binary Mixtures from Computationally Determined Flory-Huggins Interaction Parameter and Phase Diagram, 2010, 7(3), pp. 795-804) (Year: 2001).

Naumov et al, Chemical Reviews, Mechanically Responsive Molecular Crystals, 2015, 115, pp. 12440-12490. (Year: 2015).

* cited by examiner

*Primary Examiner* — Paul A Zucker

(74) *Attorney, Agent, or Firm* — Oblon, McClelland, Maier & Neustadt, L.L.P.

(57) ABSTRACT

A method is described for exfoliating a microcrystal of an anthracene derivative by irradiation with short pulses of light having a wavelength of 220-420 nm. The irradiation induces a cis-trans isomerization of the anthracene derivative in a part of the microcrystal, which leads to the separation of an outer layer having a thickness of 200-600 nm. The exfoliated microcrystal may be irradiated again with pulses of light of a same or different wavelength.

18 Claims, 27 Drawing Sheets

MICROCRYSTAL EXFOLIATION BY UV LIGHT IRRADIATION

CROSS-REFERENCE TO RELATED APPLICATIONS

This application is a continuation of Ser. No. 15/947,426, now allowed, having a filing date of Apr. 6, 2018 which is incorporated herein by reference in its entirety.

BACKGROUND OF THE INVENTION

Technical Field

The present invention relates to a method of exfoliating a microcrystal by short pulses of UV-light irradiation.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Photomechanical materials can be used to directly transform light to mechanical work. See Kim, T. et al. *Chemphyschem* 2014, 15, 400-14; Zhu, L. et al. "Photomechanical Effects in Photochromic Crystals." In *Photomechanical Materials, Composites, and Systems*; John Wiley & Sons, Ltd: Chichester, UK, 2017; pp. 233-274—each incorporated herein by reference in its entirety. While polymer-based materials that incorporate photochromic molecules have received much attention, recent work has demonstrated that molecular crystals composed solely of photochromic molecules can also deform under light exposure. See Min Lee, K.; Lynch, B. M.; Luchette, P.; White, T. J. Photomechanical effects in liquid crystal polymer networks prepared with m-fluoroazobenzene. *J. Polym. Sci. Part A Polym. Chem.* 2014, 52, 876-882, doi:10.1002/pola.27072; Eisenbach, C. D. ISOMERIZATION OF AROMATIC AZO CHROMOPHORES IN POLY(ETHYL ACRYLATE) NETWORKS AND PHOTOMECHANICAL EFFECT. *Polymer* 1980, 21, 1175-1179, doi:10.1016/0032-3861(80)90083-X; Ikeda, T.; Mamiya, J. I.; Yu, Y. Photomechanics of liquid-crystalline elastomers and other polymers. *Angew. Chemie-Int. Ed.* 2007, 46, 506-528, doi:10.1002/anie.200602372; and Matějka, L.; Ilavský, M.; Dušek, K.; Wichterle, O. Photomechanical effects in crosslinked photochromic polymers. *Polymer* 1981, 22, 1511-1515, doi:10.1016/0032-3861(81)90321-9, each incorporated herein by reference in their entirety. Such photomechanical molecular crystals can execute a variety of motions including bending, twisting, coiling, rolling, expanding, sliding of layers, and jumping. See Al-Kaysi, R. O.; Bardeen, C. J. Reversible Photoinduced Shape Changes of Crystalline Organic Nanorods. *Adv. Mater.* 2007, 19, 1276-1280, doi:10.1002/adma.200602741; Zhu, L.; Al-Kaysi, R. O.; Bardeen, C. J. Reversible photoinduced twisting of molecular crystal microribbons. *J. Am. Chem. Soc.* 2011, 133, 12569-12575, doi:10.1021/ja201925; Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi:10.1002anie.201302323; Al-Kaysi, R. O.; Miller, A. M.; Bardeen, C. J. Photochemically Driven Shape Changes of Crystalline Organic Nanorods. *J. Am. Chem. Soc.* 2006, 128, 15938-15939, doi:10.1021/ja064535p; Zhang, Y.; Peng, C.; Cui, B.; Wang, Z.; Pang, X.; Ma, R.; Liu, F.; Che, Y.; Zhao, J. Direction-Controlled Light-Driven Movement of Microribbons. *Adv. Mater.* 2016, 1-8, doi:10.1002/adma.201602411; Naumov, P.; Sahoo, S. C.; Zakharov, B. A.; Boldyreva, E. V. Dynamic single crystals: Kinematic analysis of photoinduced crystal jumping (the photosalient effect). *Angew. Chemie-Int. Ed.* 2013, 52, 9990-9995, doi:10.1002/anie.201303757; Medishetty, R.; Husain, A.; Bai, Z.; Runčevski, T.; Dinnebier, R. E.; Naumov, P.; Vittal, J. J. Single Crystals Popping Under UV Light: A Photosalient Effect Triggered by a [2+2] Cycloaddition Reaction. *Angew. Chemie Int. Ed.* 2014, 53, 5907-5911, doi:10.1002/anie.201402040; and Sahoo, S. C.; Sinha, S. B.; Kiran, M. S. R. N.; Ramamurty, U.; Dericioglu, A. F.; Reddy, C. M.; Naumov, P. Kinematic and mechanical profile of the self-actuation of thermosalient crystal twins of 1,2,4,5-tetrabromobenzene: A molecular crystalline analogue of a bimetallic strip. *J. Am. Chem. Soc.* 2013, 135, 13843-13850, doi:10.1021/ja4056323, each incorporated herein by reference in their entirety. There is considerable evidence that the crystal size and shape can have a profound effect on its photoinduced mechanical response. For example, in many cases the photomechanical crystal dimensions must be on the order of microns or less to avoid fracture or disintegration upon responding to light stimulus. In larger crystals, the build-up of internal strain due to the simultaneous presence of both reactant and product domains can lead to fracture and loss of crystal integrity. Naumov and coworkers have shown that sudden release of kinetic energy during the fracture process can propel microcrystal fragments over large distances (the photosalient phenomenon), but this process is difficult to control with fragments flying in all directions. Even for microcrystals composed of the same molecule and packing motif, different shapes can lead to different modes of mechanical motion, ranging from bending to twisting to shattering. See Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi:10.1002/anie.201302323—incorporated herein by reference in its entirety. In order to generate photoactive molecular crystals with well-defined mechanical responses, as well as identify new modes of action, it is necessary to develop methods to control crystal shape and dimensions in a reproducible manner. As an example of a new photomechanical response, if a crystal could split apart in a controlled, reproducible way, the "problem" of photoinduced fracture might become a feature that could instead be harnessed.

The use of co-precipitation of organic molecules from aqueous surfactants has proven to be a general way to prepare uniform size nano- and microcrystal suspensions of organic crystals. See Kim, T.; Zhu, L.; Al-Kaysi, R. O.; Bardeen, C. J. Organic photomechanical materials. *Chemphyschem* 2014, 15, 400-14, doi:10.1002/cphc.201300906; Zhu, L.; Tong, F.; Al-Kaysi, R. O.; Bardeen, C. J. Photomechanical Effects in Photochromic Crystals. In *Photomechanical Materials, Composites, and Systems*; John Wiley & Sons, Ltd: Chichester, UK, 2017; pp. 233-274 ISBN 9781119123279; Min Lee, K.; Lynch, B. M.; Luchette, P.; White, T. J. Photomechanical effects in liquid crystal polymer networks prepared with m-fluoroazobenzene. *J. Polym. Sci. Part A Polym. Chem.* 2014, 52, 876-882, doi:10.1002/pola.27072; Eisenbach, C. D. ISOMERIZATION OF AROMATIC AZO CHROMOPHORES IN POLY(ETHYL ACRYLATE) NETWORKS AND PHOTOMECHANICAL EFFECT. Polymer (Guild). 1980, 21, 1175-1179, doi:

10.1016/0032-3861(80)90083-X; Ikeda, T.; Mamiya, J. I.; Yu, Y. Photomechanics of liquid-crystalline elastomers and other polymers. *Angew. Chemie-Int. Ed.* 2007, 46, 506-528, doi:10.1002/anie.200602372; Matějka, L.; Ilavský, M.; Dušek, K.; Wichterle, O. Photomechanical effects in cross-linked photochromic polymers. *Polymer (Guildf).* 1981, 22, 1511-1515, doi:10.1016/0032-3861(81)90321-9; Al-Kaysi, R. O.; Bardeen, C. J. Reversible Photoinduced Shape Changes of Crystalline Organic Nanorods. *Adv. Mater.* 2007, 19, 1276-1280, doi:10.1002/adma.200602741; Zhu, L.; Al-Kaysi, R. O.; Bardeen, C. J. Reversible photoinduced twisting of molecular crystal microribbons. *J. Am. Chem. Soc.* 2011, 133, 12569-12575, doi:10.1021/ja201925p; Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi: 10.1002/anie.201302323; Al-Kaysi, R. O.; Müller, A. M.; Bardeen, C. J. Photochemically Driven Shape Changes of Crystalline Organic Nanorods. *J. Am. Chem. Soc.* 2006, 128, 15938-15939, doi:10.1021/ja064535p; Zhang, Y.; Peng, C.; Cui, B.; Wang, Z.; Pang, X.; Ma, R.; Liu, F.; Che, Y.; Zhao, J. Direction-Controlled Light-Driven Movement of Microribbons. *Adv. Mater.* 2016, 1-8, doi: 10.1002/adma.201602411; Naumov, P.; Sahoo, S. C.; Zakharov, B. A.; Boldyreva, E. V. Dynamic single crystals: Kinematic analysis of photoinduced crystal jumping (the photosalient effect). *Angew. Chemie-Int. Ed.* 2013, 52, 9990-9995, doi: 10.1002/anie.201303757; Medishetty, R.; Husain, A.; Bai, Z.; Runčevski, T.; Dinnebier, R. E.; Naumov, P.; Vittal, J. J. Single Crystals Popping Under UV Light: A Photosalient Effect Triggered by a [2+2] Cycloaddition Reaction. *Angew. Chemie Int. Ed.* 2014, 53, 5907-5911, doi:10.1002/anie.201402040; Sahoo, S. C.; Sinha, S. B.; Kiran, M. S. R. N.; Ramamurty, U.; Dericioglu, A. F.; Reddy, C. M.; Naumov, P. Kinematic and mechanical profile of the self-actuation of thermosalient crystal twins of 1,2,4, 5-tetrabromobenzene: A molecular crystalline analogue of a bimetallic strip. *J. Am. Chem. Soc.* 2013, 135, 13843-13850, doi:10.1021/ja4056323; Zhang, X.; Zhang, X.; Zou, K.; Lee, C.-S.; Lee, S.-T. Single-crystal nanoribbons, nanotubes, and nanowires from intramolecular charge-transfer organic molecules. *J. Am. Chem. Soc.* 2007, 129, 3527-32, doi:10.1021/ja0642109; Lu, L. T.; Tung, L. D.; Robinson, I.; Ung, D.; Tan, B.; Long, J.; Cooper, A. I.; Fernig, D. G.; Thanh, N. T. K. Size and shape control for water-soluble magnetic cobalt nanoparticles using polymer ligands. *J. Mater. Chem.* 2008, 18, 2453; Bakshi, M. S.; Sachar, S.; Kaur, G.; Bhandari, P.; Kaur, G.; Biesinger, M. C.; Possmayer, F.; Petersen, N. O. Dependence of crystal growth of gold nanoparticles on the capping behavior of surfactant at ambient conditions. *Cryst. Growth Des.* 2008, 8, 1713-1719, doi:10.1021/cg8000043; Xiao, J.; Qi, L. Surfactant-assisted, shape-controlled synthesis of gold nanocrystals. *Nanoscale* 2011, 3, 1383, doi: 10.1039/c0nr00814a; Zhang, X.; Dong, C.; Zapien, J.; Ismathullakhan, S.; Kang, Z.; Jie, J.; Zhang, X.; Chang, J.; Lee, C.-S.; Lee, S.-T. Polyhedral Organic Microcrystals: From Cubes to Rhombic Dodecahedra. *Angew. Chemie Int. Ed.* 2009, 48, 9121-9123, doi:10.1002/anie.200902929; Tian, B.; Zhang, X.; Yu, C.; Zhou. M.; Zhang, X. The aspect ratio effect of drug nanocrystals on cellular internalization efficiency, uptake mechanisms, and in vitro and in vivo anticancer efficiencies. *Nanoscale* 2015, 7, 3588-3593, doi: 10.1039/C4NR06743F; Zhao, C.; Zhang, X.; Zhang, Y.; Xing, Y.; Zhang, X.; Zhang, X.; Jie, J. Facile formation of microscale hollow superstructures made of organic nanocrystals and their application as a humidity sensor. *CrystEngComm* 2012, 14, 819-823, doi:10.1039/C1CE06139A; Yang, S.; Lin, Z.; Shi, N.; Jin, L.; Yu, M.; Xie, L.; Yi, M.; Huang, W. A polyhedral supramolecular system of endocyclic crystalline organic nanostructures: the case of triptycenes. *CrystEngComm* 2015, 17, 1448-1452, doi:10.1039/ C4CE02379J; Li, W.; Zhang, X.; Hao, X.; Jie, J.; Tian, B.; Zhang, X. Shape design of high drug payload nanoparticles for more effective cancer therapy. *Chem. Commun.* 2013, 49, 10989, doi:10.1039/c3cc46718j; Zhang, X.; Zhao, C.; Lv, J.; Dong, C.; Ou, X.; Zhang, X.; Lee, S. Crystal Structure Origin for Shape-Dependent Emission of 2,5,8,11-Tetra-tert-butylperylene Micro-/Nanocrystals. *Cryst. Growth Des.* 2011, 11, 3677-3680, doi:10.1021/cg200159w; Joshi, S. Crystal Habit Modification Using Habit Modifiers. *Mod. Asp. Bulk Cryst. Thin Film Prep.* 2012, 413-436, doi: 10.1016/0022-0248(75)90066-4; Zhang, X.; Zhang, X.; Shi, W.; Meng, X.; Lee, C.; Lee, S. Morphology-controllable synthesis of pyrene nanostructures and its morphology dependence of optical properties. *J. Phys. Chem. B* 2005, 109, 18777-18780, doi:10.1021/jp052385j; Fu, H.; Xiao, D.; Yao, J.; Yang, G. Nanofibers of 1,3-diphenyl-2-pyrazoline induced by cetyltrimethylammonium bromide micelles. *Angew. Chemie-Int. Ed.* 2003, 42, 2883-2886, doi:10.1002/ anie.200350961; Maity, A.; Mazumdar, P.; Samanta, S.; Das, D.; Shyamal, M.; Sahoo, G. P.; Misra, A. Morphology directing synthesis of 1-aminopyrene microstructures and its super quenching effect towards nitro aromatics. *J. Mol. Liq.* 2016, 221, 358-367, doi:10.1016/j.molliq.2016.06.012; Wang, J.; Liao, Q.; Chen, H.; Yang, D.; Gao, Y.; Li, H. Polymer-assisted fabrication of crystalline rectangular microtubes of triphenylimidazole derivatives. *CrystEngComm* 2012, 14, 5517, doi:10.1039/c2ce25068c; Liu, Q.; Zhou. H.; Zhu, J.; Yang, Y.; Liu, X.; Wang, D.; Zhang, X.; Zhuo, L. Self-assembly into temperature dependent micro-/ nano-aggregates of 5,10,15,20-tetrakis(4-carboxyl phenyl)-porphyrin. *Mater. Sci. Eng. C* 2013, 33, 4944-4951, doi: 10.1016/j.msec.2013.08.015; Yu, H.; Qi, L. Polymer-assisted crystallization and optical properties of uniform microrods of organic dye Sudan I I. *Langmir* 2009, 25, 6781-6786, doi:10.1021/la900296y; Zhang, X.; Zhang, X.; Yuan, G.; Li, Q.; Wang, B.; Zhang, R.; Chang, J. C.; Lee, C. S.; Lee, S. T. Single-crystal 9,10-diphenylanthracene nanoribbons and nanorods. *Chem. Mater.* 2008, 20, 6945-6950, doi:10.1021/cm801896r; Ibe, S.; Ise, R.; Oaki, Y.; Imai, H. Twisted growth of organic crystal in a polymer matrix: sigmoidal and helical morphologies of pyrene. *CrystEngComm* 2012, 14, 7444, doi:10.1039/c2ce26079d; Lai, Y.; Li, H.; Pan, J.; Guo, J.; Kang, L.; Cao, Z. Synthesis of Ultrathin Nanosheets of Perylene. *Cryst. Growth Des.* 2015, 15, 1011-1016, doi:10.1021/cg5015016; Saini, A.; Justin Thomas, K. R. Bis-naphthalimides bridged by electron acceptors: optical and self-assembly characteristics. *RSC Adv.* 2016, 6, 71638-71651, doi:10.1039/C6RA12776B; Wang, H.; Zhang, W.; Gao, C. Shape Transformation of Light-Responsive Pyrene-Containing Micelles and Their Influence on Cytoviability. *Biomacromolecules* 2015, 16, 2276-2281, doi:10.1021/acs.biomac.5b00497; Qiu, Y.; Chen, P.; Liu, M. Evolution of various porphyrin nanostructures via an oil/aqueous medium: Controlled self-assembly, further organization, and supramolecular chirality. *J. Am. Chem. Soc.* 2010, 132, 9644-9652, doi:10.1021/ja1001967; Yu, D.; Zhang, Q.; Wu, C.; Wang, Y.; Peng, L.; Zhang, D.; Li, Z.; Wang, Y. Highly Fluorescent Aggregates Modulated by Surfactant Structure and Concentration. *J Phys. Chem. B* 2010, 114, 8934-8940, doi:10.1021/jp102742a; Gu, X.; Yao, J.; Zhang, G.; Zhang, D. Controllable Self-Assembly of Di(p-methoxylphenyl)Dibenzofulvene into Three Different Emission Forms. *Small* 2012, 8, 3406-3411, doi:10.1002/ smll.201201334; Peng, L.; Chen, Y.-N.; Qiang Dong, Y.; He, C.; Wang, H. Surfactant-assisted self-assembled polymorphs of AIEgen di(4-propoxyphenyl)dibenzofulvene. *J. Mater. Chem. C* 2017, doi:10.1039/C6TC04616A; Lei, Y.; Liao, Q.; Fu, H.; Yao, J. Phase- and Shape-Controlled Synthesis of Single Crystalline Perylene Nanosheets and Its Optical Properties. *J. Phys. Chem. C* 2009, 113, 10038-10043, doi:10.1021/jp901357t; Zhou, D.; Li, Y.; Wang, J.; Xu, P.; Han, X. Synthesis of polyaniline nanofibers with high electrical conductivity from CTAB-SDBS mixed surfactants. *Mater. Lett.* 2011, 65, 3601-3604, doi:10.1016/j.matlet.2011.08.021; Kang, L.; Wang, Z.; Cao, Z.; Ma, Y.; Fu, H.; Yao, J. Colloid Chemical Reaction Route to the Preparation of Nearly Monodispersed Perylene Nanoparticles: Size-Tunable Synthesis and Three-Dimensional Self-Organization. *J. Am. Chem. Soc.* 2007, 129, 7305-7312, doi:10.1021/ja068710d; Fery-Forgues, S.; Veesler, S.; Fellows, W. B.; Tolbert, L. M.; Solntsev, K. M. Microcrystals with Enhanced Emission Prepared from Hydrophobic Analogues of the Green Fluorescent Protein Chromophore via Reprecipitation. *Langmuir* 2013, 29, 14718-14727, doi: 10.1021/la403909k; Anthony, S. P.; Draper, S. M. Nano/Microstructure Fabrication of Functional Organic Material: Polymorphic Structure and Tunable Luminescence. *J. Phys. Chem. C* 2010, 114, 11708-11716, doi:10.1021/jp100594w; Kim, F. S.; Ren, G.; Jenekhe, S. A. One-Dimensional Nanostructures of π-Conjugated Molecular Systems: Assembly, Properties, and Applications from Photovoltaics, Sensors, and Nanophotonics to Nanoelectronics †. *Chem. Mater.* 2011, 23, 682-732, doi:10.1021/cm102772x; and Lin, Z.-Q.; Sun, P.-J.; Tay, Y.-Y.; Liang, J.; Liu, Y.; Shi, N.-E.; Xie, L.-H.; Yi, M.-D.; Qian, Y.; Fan, Q.-L.; Zhang, H.; Hng, H. H.; Ma, J.; Zhang, Q.; Huang, W. Kinetically Controlled Assembly of a Spirocyclic Aromatic Hydrocarbon into Polyhedral Micro/Nanocrystals. ACS Nano 2012, 6, 5309-5319, doi:10.1021/nn3011398, each incorporated herein by reference in their entirety. Several groups have shown that varying parameters like concentration, temperature, and nature of surfactant can lead to the growth of crystals with different shapes and faceting. In the present disclosure, a divinyl anthracene derivative (cis-DMAAM) that can undergo a cis-trans photoisomerization reaction in both solution and in its crystal form was chosen as the photomechanical active element. Both the cis and trans isomerization reactions lead to an amorphous mixture that has very different properties than the single component reactant. Nanowires, with a diameter less than 200 nm, made from the cis or trans-DMAAM spontaneously coil to a dot when pulsed with visible 475 nm light. See Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi: 10.1002/anie.201302323—incorporated herein by reference in its entirety.

In view of the foregoing, one objective of the present invention is to provide a method of harnessing a type of photomechanical response based on a different crystal morphology of an anthracene derivative. As described herein, crystal growth conditions are tuned to control the faceting in molecular crystals composed of the anthracene derivative. This leads to block-like or tetragonal microcrystals that undergo spontaneous delamination (peeling) after a brief pulse of 220-420 nm light. This process can be repeated multiple times on the same µ-block, uniformly peeling off a layer with every pulse of light. In addition to demonstrating a novel photomechanical effect made possible by control of crystal shape and faceting, the repetitive photoinduced delamination may also be used in novel materials with photo-renewable surfaces, or for various other applications.

BRIEF SUMMARY OF THE INVENTION

According to a first aspect, the present disclosure relates to a method of exfoliating a microcrystal. The method involves irradiating a compound of formula I in the form of a microcrystal with light having a wavelength of 220-420 nm, where formula I is,

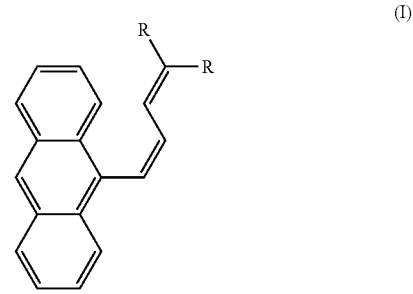

wherein each R is independently an optionally substituted alkyl group, an optionally substituted cycloalkyl group, an optionally substituted heterocyclyl group, an optionally substituted aryl group, an optionally substituted heteroaryl group, an optionally substituted arylalkyl group, an optionally substituted ester group, an optionally substituted carboxyl group, or an optionally substituted alkoxy group. Irradiation induces in a portion of the microcrystal a cis-trans isomerization of formula I to formula II, where formula II is

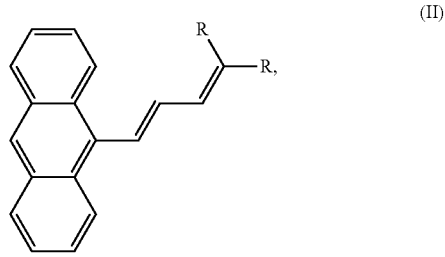

and the irradiating separates an outer layer from the microcrystal to produce an exfoliated microcrystal, the outer layer having a thickness of 200-600 nm, dependent on the duration of the light pulse. Short pulses give thinner exfoliated layers while longer pulses can lead to very thick exfoliated layers that can basically split the crystal in half along the long axis.

In one embodiment, the compound comprises at least 70 wt % formula I in crystalline form, relative to a total weight of the microcrystal.

In one embodiment, the outer layer is amorphous.

In one embodiment, the irradiating involves an exposure time of 0.4-2.0 s.

In one embodiment, the light has a power density of 1-200 mW/cm$^2$.

In one embodiment, the irradiating involves exposure to sunlight.

In one embodiment, each R is the same formula group.

In one embodiment, formula I is cis-dimethyl-2(3-(anthracen-9-yl)allylidene)malonate and formula II is trans-dimethyl-2(3-(anthracen-9-yl)allylidene)malonate.

In one embodiment, the microcrystal is on an exterior surface of an object.

In one embodiment, the microcrystal is a component of an adhesive.

In one embodiment, the microcrystal is a component of an implant or orthopedic device.

In one embodiment, the microcrystal is a component of a photosensitive switch.

In one embodiment, the method also involves the step of irradiating the exfoliated microcrystal with light having a wavelength of 220-750 nm to produce a second exfoliated microcrystal and a second layer having a thickness of 200-600 nm.

In one embodiment, the microcrystal is a component of a composition that comprises a dye or a pigment.

In one embodiment, the microcrystal is in the form of a rectangular block having a longest linear dimension of 1-300 µm and an aspect ratio of 1:1-10:1.

In a further embodiment, the microcrystal is in the form of a square cuboid.

In a further embodiment, the microcrystal is dispersed within a solution comprising a surfactant.

In a further embodiment, a larger microcrystal is formed by seeding a super saturated solution of dissolved formula I in aqueous surfactant, with a smaller crystal of formula I.

In a further embodiment, this crystal of formula I has an octahedral form.

In a further embodiment, the compound of formula I is produced by irradiating a compound of formula II with light having a visible wavelength.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
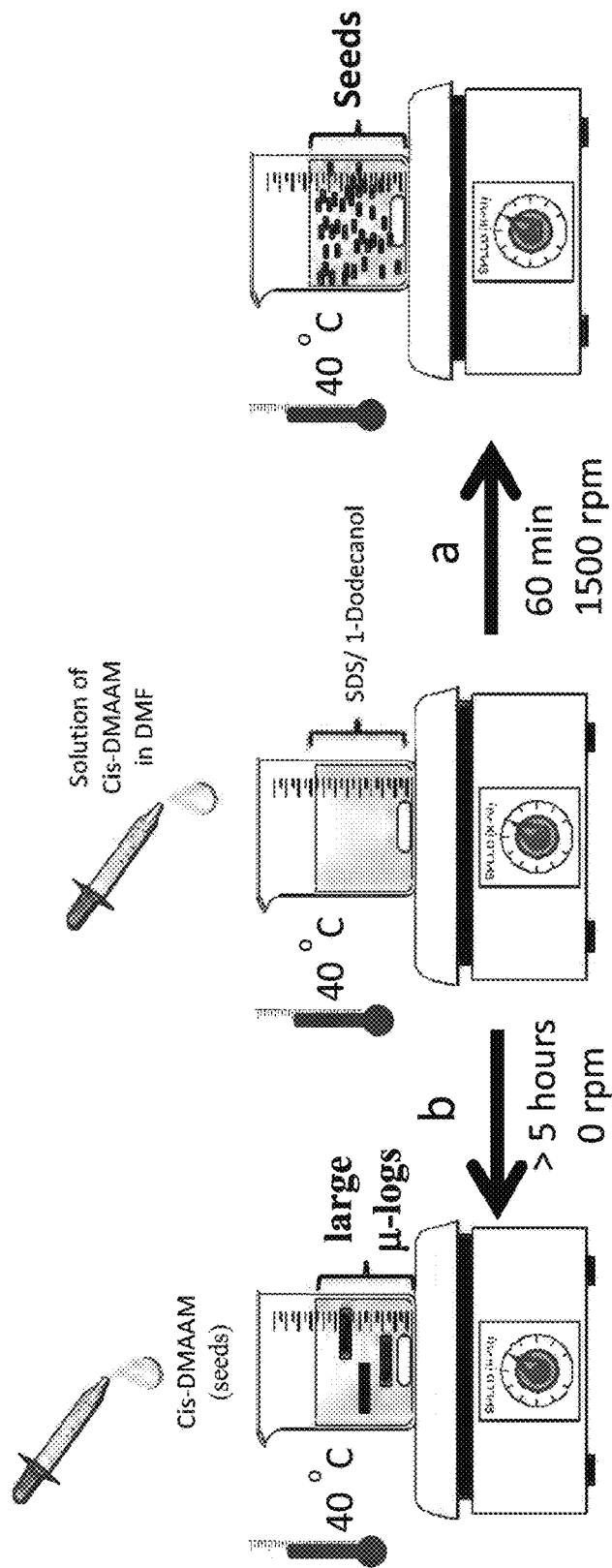
FIG. 1 is a schematic for making cis-DMAAM µ-logs (seeds) and larger cis-DMAAM µ-logs.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more."

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

As used herein, "particle size" and "pore size" may be thought of as the lengths or longest dimensions of a particle and of a pore opening, respectively.

For polygonal shapes, the term "length," as used herein, and unless otherwise specified, refers to the greatest possible distance measured along a side of the polygonal shape. For a circle, an oval, and an ellipse, "length" refers to the greatest possible distance measured from one point on the shape through the center of the shape to a point directly across from it. The term "width" as used herein, and unless otherwise specified, refers to the greatest possible distance perpendicular to the length. "Diameter" may be thought of as width.

The present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{17}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

According to a first aspect, the present disclosure relates to a method of exfoliating a microcrystal by irradiating a compound of formula I in the form of a microcrystal, where formula I is,

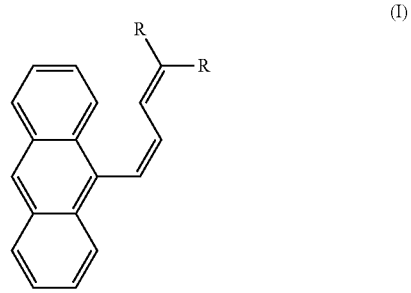

wherein each R is independently an optionally substituted alkyl group, an optionally substituted cycloalkyl group, an optionally substituted heterocyclyl group, an optionally substituted aryl group, an optionally substituted heteroaryl group, an optionally substituted arylalkyl group, an ester group, a carboxyl group, a cyano group, or an optionally substituted alkoxy group.

The term "substituted," as used herein in reference to a moiety, means that one or more, especially up to five, more especially one, two, or three, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognized by a person having ordinary skill in the art.

The term "alkyl," as used herein, unless otherwise specified, refers to a saturated straight, branched, or cyclic, primary, secondary, or tertiary hydrocarbon of typically $C_1$ to $C_8$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, nitro, amide, halogen, alkylamino, heterocyclic, aryl, carboxylic acid, ester, ketone, arylamino, alkoxy, cycloalkyl, aryloxy, nitro, cyano, sulfonic acid, sulfonamide, sulfate, phosphonic acid, phosphate, and phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference in its entirety.

The term "cycloalkyl," as used herein, refers to an aliphatic cyclic hydrocarbon group, preferably containing three to eight carbon atoms. The term includes both substituted and unsubstituted moieties. Examples of cycloalkyl groups include, but are not limited to, cyclopropyl, cyclobutyl, cyclopentyl, and cyclohexyl. The cycloalkyl group can be substituted with one or more moieties selected from the group consisting of hydroxyl, amino, halogen, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference in its entirety.

The term "heterocyclyl," as used herein, refers to an aliphatic, partially unsaturated or fully saturated, 3- to 14-membered ring system, including single rings of three to eight carbon atoms and bi- and tricyclic ring systems, which contains at least one heteroatom independently selected from oxygen, nitrogen, and sulfur. Heterocyclyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The heterocyclyl group can be substituted with one or more moieties selected from the group consisting of hydroxyl, amino, halogen, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference in its entirety.

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, halogen, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference in its entirety.

The term "heteroaryl," as used herein, refers to an aromatic monocyclic, fused bicyclic, and fused tricyclic ring systems, wherein at least one atom is selected from the group consisting of oxygen, nitrogen, and sulfur. Heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, and benzothiazolyl. The heteroaryl group can be substituted with one or more moieties selected from the group consisting of hydroxyl, amino, halogen, alkylamino, arylamino, alkoxy, aryloxy, nitro, cyano, sulfonic acid, sulfate, phosphonic acid, phosphate, or phosphonate, either unprotected, or protected as necessary, as to known to those skilled in the art, for example, as taught in Greene, et al., "Protective Groups in Organic Synthesis," John Wiley and Sons, Second Edition, 1991, hereby incorporated by reference in its entirety.

The term "arylalkyl," as used herein, refers to an aryl-substituted alkyl group, such as benzyl, phenethyl, and 1-naphthylethyl.

The term "ester," as used herein, refers to a group of formula "—C(O)OR$^x$," wherein R$^x$ is alkyl, cycloalkyl, heterocyclyl, aryl, heteroaryl, arylalkyl, or some other group mentioned herein.

The term "carboxyl", as used herein, represents a group of formula "—COOH," and may also be considered as a carboxylic acid group.

The term "cyano", as used herein, represents a group of formula "—CN."

The term "alkoxyl," as used herein, refers to an alkyl-O— group wherein alkyl is as previously described. Example groups include, but are not limited to, methoxyl, ethoxyl, propoxyl, isopropoxyl, butoxyl, i-butoxyl, and pentoxyl.

In one embodiment, both R groups of formula I have the same identities. Preferably both R groups are cyano groups, ester groups, carboxyl groups, or carboxylic acid groups. In a further embodiment, both R groups are methylester groups of the formula "—C(O)OCH$_3$." In this embodiment, formula I is cis-dimethyl-2(3-(anthracen-9-yl)allylidene)malonate, and may also be denoted as (Z)-dimethyl-2(3-(anthracen-9-yl)allylidene)malonate or cis-DMAAM.

The irradiating induces in a portion of the microcrystal a cis-trans isomerization of formula I to formula II, where formula II is

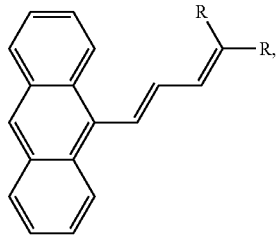

(II)

wherein each R is independently a group as previously described for formula I. Similarly, in one embodiment, formula II comprises R where both represent the same group. In another embodiment, formula II comprises R where each group represents a different group.

In one embodiment, the R groups may be chosen so that formula I and/or formula II have specific colors. In another embodiment, the R groups may be chosen so that formula I and formula II interact differently with a separate pigment or dye, or with components of an adhesive.

In one embodiment, both R groups of formula II have the same identities. Preferably both R groups are cyano groups, ester groups, carboxyl groups, or carboxylic acid groups. In a further embodiment, both R groups are methylester groups of the formula "—C(O)OCH₃." In this embodiment, formula II is trans-dimethyl-2(3-(anthracen-9-yl)allylidene)malonate, and may also be denoted as (E)-dimethyl-2(3-(anthracen-9-yl)allylidene)malonate, or trans-DMAAM.

In one embodiment, both R groups of formula I may have the same identities, and by extension, both R groups of formula II in this embodiment would have the same identities to each other and the R groups of formula I. In a preferred embodiment, formula I is cis-dimethyl-2(3-(anthracen-9-yl)allylidene)malonate, or cis-DMAAM, as shown in (III), and formula II is trans-dimethyl-2(3-(anthracen-9-yl)allylidene)malonate, or trans-DMAAM, as shown in (IV). In another embodiment, formula I is cis-2-(3-(anthracen-9-yl)allylidene)malononitrile, or cis-9DVAM, and formula II is trans-2-(3-(anthracen-9-yl)allylidene)malononitrile, or trans-9DVAM. Cis-9DVAM (cis-2-(3-(anthracen-9-yl)allylidene)malononitrile) may be denoted as (Z)-9DVAM ((Z)-2-(3-(anthracen-9-yl)allylidene)malononitrile), and trans-9DVAM (trans-2-(3-(anthracen-9-yl)allylidene)malononitrile) may be denoted as (E)-9DVAM ((E)-2-(3-(anthracen-9-yl)allylidene)malononitrile).

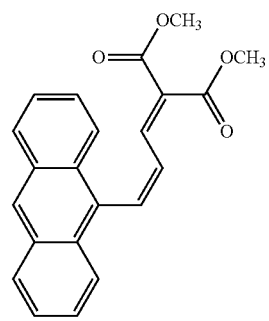

(III)

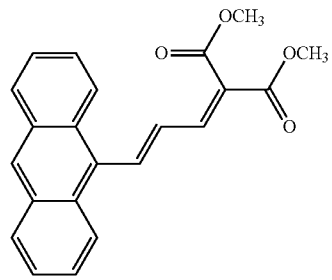

(IV)

In one embodiment, the R groups of formula I may have different identities, and by extension, the R groups of formula II may also have different identities.

In one embodiment, the photo-isomerization between formula I and formula II may be represented by Equation I:

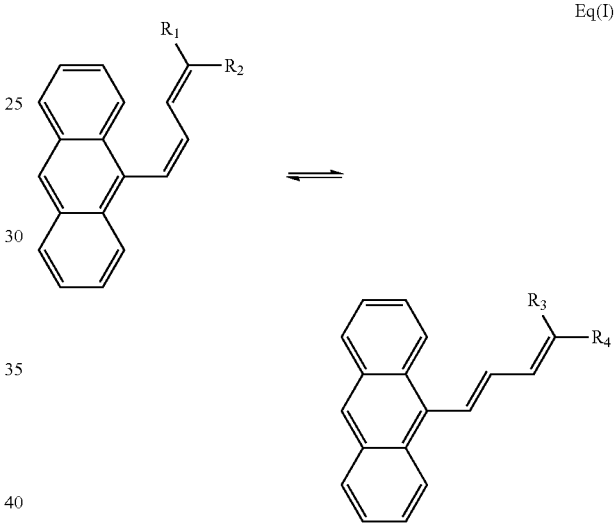

Eq(I)

As previously stated, in one embodiment, $R_1=R_2=R_3=R_4$. In another embodiment, where $R_1$ and $R_2$ represent different groups, $R_3$ may be the same group as $R_1$, and $R_4$ may be the same group as $R_2$. However, in another embodiment where $R_1$ and $R_2$ represent different groups, $R_3$ may be the same group as $R_2$, and $R_4$ may be the same group as $R_1$.

Formula I and formula II may be referred to as anthracene derivatives, with the allylidene attached at the 9 carbon of anthracene. In an alternative embodiment, formula I and II may be an anthracene derivative with the allylidene attached at a different carbon, such as carbon 1, 2, or 3, by the conventional carbon numbering. In another alternative embodiment, two or more alkylidenes may be attached to a single anthracene. In another embodiment, the anthracene may have an allylidene and one or more substituted groups on the anthracene rings, where the substituted groups may be any of those previously listed for R. In another embodiment, an alternative form of formula I and II may be a benzene derivative, a naphthalene derivative, a stilbenoid derivative, a diphenyl methane derivative or some derivative of a polycyclic aromatic hydrocarbon, including, but not limited to phenanthrene, tetracene, pyrene, pentacene, fluorine, and benzo[c]fluorine. In these embodiments, the alternative formula I and formula II may be able to isomerize from one isomer to another using light irradiation of the same frequency. In another embodiment, the alternative formula I and II may reversibly isomerize from one to the other using different wavelengths of light, which is considered P-type reversibility. In another embodiment, the alternative formula I or II may reversibly isomerize to one form upon irradiation, and then isomerize back to its s original form without irradiation. This type of thermally-driven reversibility may be called T-type reversibility.

In one embodiment, the microcrystal is in the form of a rectangular block having a longest linear dimension, or length, of 1-300 μm, preferably 3-200 μm, more preferably 5-100 μm, more preferably 6-25 μm. However, in some embodiments, the microcrystal may be in the form of a rectangular block with a longest linear dimension of less than 1 μm or greater than 300 μm. A crystal having a longest linear dimension of less than 1 μm may be considered a nanocrystal or nanoparticle. In one embodiment, the microcrystal may have an aspect ratio of 1:1-10:1, preferably 1.5:1-8:1, more preferably 2:1-7:1. As defined here, the aspect ratio is the ratio of the longest dimension to the second longest dimension. Preferably the second longest dimension is perpendicular to the longest dimension. However, in some embodiments, the aspect ratio may be greater than 10:1, and the microcrystal in this elongated form may be considered a microwire, a nanowire, a fiber, or microwhisker.

In one embodiment, the microcrystal is in the form of a cuboid. As defined here, a cuboid is a convex polyhedron bounded by six quadrilateral faces and having a polyhedral graph that is the same as a cube. The microcrystal may also be referred to as a microblock, μ-block, microlog, or μ-log, due to this shape. The microcrystal having a cuboid form may further be in the form of a rectangular cuboid, where all angles are right angles, and opposite faces of the shape are equal. A rectangular cuboid may also be considered a right rectangular prism, a rectangular parallelepiped, or an orthogonal parallelepiped.

In one embodiment, the microcrystal is in the form of a square cuboid, which is a rectangular cuboid where at least two faces are squares. This form may also be called a square box, or a right square prism. In another embodiment, the microcrystal may be in the form of a square cuboid, but with beveled edges or corners at either or both ends. In a related embodiment, this form may be considered as the microcrystal having octahedral-shaped ends, or pyramidal-shaped ends. In another embodiment, the microcrystal may be in the form of a square cuboid, but with an opening or pore on either or both ends. In one embodiment, the microcrystal may be hollow, with an opening or pore on either or both ends. The opening or pore may have a pore size of 400-1000 nm, preferably 500-800 nm, and a depth of 5-70%, preferably 10-60%, more preferably 15-55% of the length of the microcrystal.

In alternative embodiments, formula I may be formed into a crystal having a different shape, for example, as an elongated nanowire or microwire having a width of 500 nm-2 μm, preferably 800 nm-1.5 μm, and a length of 12-100 μm, preferably 15-90 μm, more preferably 17-85 μm. However, in one embodiment, a crystal in the form of an elongated nanowire or microwire may have a length longer than 100 μm, for instance, 200-500 μm, or 220-300 μm.

In other alternative embodiments, formula I may be formed into more shapes, with or without crystalline character, such as spheres, cylinders, boxes, spikes, flakes, plates, ellipsoids, toroids, stars, ribbons, discs, rods, granules, prisms, cones, or some other shape.

As defined here, exfoliating a microcrystal refers to making an outer face or layer of a microcrystal become separate. This process may be caused by a change in crystal packing or density. The exfoliating may also be described as peeling, deforming, fracturing, flaking, shedding, splitting, shredding, scaling, blistering, chipping, delaminating, slicing, stripping, paring, or tearing. The exfoliating produces an exfoliated microcrystal and an outer layer. The outer layer may also be called a peel, a face, a flake, a slab, or a platelet. In one embodiment, the outer layer is considerably smaller than the microcrystal. For instance, the peel or flake may have a volume which is 0.1-25 vol %, preferably 0.5-20 vol %, more preferably 1-10 vol % relative to the volume of the exfoliated microcrystal. However, in some embodiments, the peel or flake may have a volume percentage smaller than 0.1 vol % or larger than 25 vol %. In one instance, a microcrystal that is small, or has a volume decreased by previous exfoliating, may produce a peel or a flake having a volume that is 50-100 vol %, or 60-80 vol % relative to a volume of the exfoliated microcrystal. In one embodiment, the exfoliating may produce more than one flake or peel simultaneously, from the same face of the microcrystal or from different faces.

In one embodiment, the microcrystal comprises at least 70 wt % formula I in crystalline form, preferably at least 80 wt % formula I in crystalline form, more preferably at least 90 wt % formula I in crystalline form, relative to a total weight of the microcrystal. In one embodiment, the microcrystal may comprise about 100 wt % formula I in crystalline form. However, in alternative embodiments, the microcrystal may comprise less than 70 wt % formula I in crystalline form relative to a total weight of the crystal.

In one embodiment, the microcrystal may comprise 0-30 wt % formula II in crystalline form, preferably 0-20 wt % formula II in crystalline form, more preferably 0-10 wt % formula II in crystalline form, relative to a total weight of the microcrystal.

In one embodiment, the compound may be considered amorphous, rather than being in the form of a microcrystal. The compound in an amorphous form may comprise formula I, formula II, or a mixture of both, for example, the mass ratio of formula I to formula II may be in the range of 1:100-100:1, preferably 1:10-10:1.

In another related embodiment, the microcrystal may consist essentially of formula I and/or formula II. As defined here, the microcrystal consisting essentially of formula I and/or formula II means that 95-100%, preferably 96.0-99.7%, more preferably 97.5-99.5% of the mass of the microcrystal is formula I and/or formula II. Where the microcrystal consists of less than 100% formula I and/or formula II, the microcrystals may have adsorbed, reacted, or incorporated contaminants, for instance from gas molecules, water, alcohols, DMF, surfactant, or other organic compounds, including derivatives of formula I or II. In an alternative embodiment, the microcrystal may be intentionally modified or incorporated with other compounds. For example, the microcrystal may comprise 0.01-3 wt %, preferably 0.1-2 wt % salt or surfactant, relative to a total weight of the microcrystal, in order to provide stability. As another example, the surface of the microcrystal may be decorated with chromophores, fluorophores, or photo-active nanoparticles to direct light irradiation and improve isomerization efficiency.

In one embodiment, the irradiating separates an outer layer from the microcrystal to produce an exfoliated microcrystal. The outer layer has a thickness of 200-600 nm, preferably 250-550 nm, more preferably 300-500 nm, even more preferably 350-450 nm, or about 400 nm. However, in other embodiments, the outer layer may have a thickness of less than 200 nm or greater than 600 nm. In some embodiments, the outer layer may be called a nanopeel, and the outer layer may be curved, or straight and planar. Preferably the outer layer comprises a mixture of formula I and formula II, at a mass ratio of formula I to formula II of 1:100-100:1, preferably 1:50-12:1, more preferably 1:10-10:1. In some embodiments, a microcrystal may fracture into two pieces, and those two pieces may both be considered microcrystals or outer layers/nanopeels if their sizes are similar, otherwise the smaller piece may be considered the outer layer with the larger piece being considered the exfoliated microcrystal. In one embodiment, the outer layer may have a face similar in size to a face of the exfoliated crystal. In another embodiment, the outer layer may have a face that is much smaller, for instance, 10-50%, preferably 20-40% of the area of the face of the microcrystal from which the outer layer originated.

In one embodiment, the outer layer is amorphous, meaning that at least 80 wt %, preferably at least 90 wt %, of the outer layer, relative to a total weight of the outer layer, does not have a crystalline packing form. This degree of crystallinity may be determined by NMR, XRD, TEM, or other techniques. However, in alternative embodiments, an outer layer may comprise more than 20 wt % or more than 50 wt % of a crystalline packing form, where the crystalline packing form comprises formula I and/or formula II. In some embodiments, depending on the morphology and size of the microcrystal, a light irradiation may only need to induce an isomerization in just a small proportion of an outer layer in order to exfoliate the microcrystal.

In one embodiment, the irradiating involves exposing the microcrystal to light for a certain exposure time. The light source may be a mercury or xenon gas discharge lamp, an electric arc, sunlight, a light emitting diode (LED), a continuous or pulsed laser, a fluorescent lamp, a cathode ray tube, or some other source. In one embodiment, filters, reflectors, collimators, fiber optics, polarizers, and/or lenses may be used to manipulate the light path or properties of the light from the light source. For example, one or more reflectors may be used to focus the light from a mercury gas discharge lamp onto the microcrystal, or into a solution containing one or more microcrystals. Alternatively, a reflector may be positioned on a side opposite the light source in order to reflect stray light back towards the microcrystal. In one embodiment, two or more light sources may be used, which may be of the same type or different types, and may be positioned on the same side or on different sides of the microcrystal. As another example, where sunlight is used as a light source, the sunlight may be filtered, reflected, and focused onto the microcrystal to increase the proportion of UV light intensity while minimizing heating and radiation from other wavelengths. For instance, a Wood's glass optical filter or a bandpass filter (475 nm, 405 nm, or 365 nm) may be used to allow UV light to pass while blocking other wavelengths.

In one embodiment, the light has a wavelength of 220-420 nm, preferably 250-410 nm, more preferably 300-405 nm. In one embodiment, the light has a wavelength of about 405 nm, though in other embodiments, the light may have a wavelength of less than 220 nm or greater than 420 nm.

In one embodiment, the light has a power density of 1-200 mW/cm$^2$, preferably 5-150 mW/cm$^2$, more preferably 40-110 mW/cm$^2$. However, in some embodiments, the light may have a power density of less than 1 mW/cm$^2$ or greater than 200 mW/cm$^2$.

In one embodiment, the exposure time may be 0.4-2.0 s, preferably 0.5-1.8 s, more preferably 0.8-1.2 s, or about 1.0 s. However, in some embodiments, the exposure time may be shorter than 0.4 s or longer than 2.0 s. For instance, in one embodiment, the exposure time may be at least 1 min, at least 10 min, or at least 60 min, in order to convert a larger proportion of formula I to formula II. In one embodiment, the exposure time may be essentially continuous. In other embodiments, shorter exposure times may be combined with greater power densities, or longer exposure times may be combined with lower power densities. A person having ordinary skill in the art may be able to determine advantageous irradiation conditions, which may depend on the crystal size and morphology.

In one embodiment, a longer exposure time may lead to the formation of thicker outer layers, while a shorter exposure time may lead to the formation of thinner outer layers. In general, an outer layer may not separate immediately following the irradiation, though in alternative embodiments, an outer layer may separate during or within 2 s of the end of the exposure. In one embodiment, the outer layer may separate 10-30 s after the irradiating, preferably 12-25 s after the irradiating, more preferably 13-20 s after the irradiating, though in some embodiments, the outer layer may separate 2-10 s after the irradiating, or more than 30 s after the irradiating.

In one embodiment, the microcrystal peeling or exfoliation may be observed with an optical microscope in bright field, transmitted, polarized, phase contrast, or dark field modes. In alternative embodiments, fluorescence microscopy or reflection interference contrast microscopy may be employed. Microcrystals observed by an optical microscope may also be readily available for irradiation by modifying the microscope's filters or illumination.

In one embodiment, the microcrystal is dispersed within a solution comprising a surfactant. Preferably the solution is an aqueous solution. The solution may comprise the surfactant at a vol % concentration of 0.01-5 vol %, 0.1-4 vol %, more preferably 0.3-3 vol % relative to a total volume of the aqueous solution. However, in some embodiments, the aqueous solution may comprise less than 0.01 vol % or greater than 5 vol % surfactant. The surfactant may be an ionic surfactant, a nonionic surfactant, a biological surfactant, or some other type of surfactant.

Exemplary ionic surfactants include, but are not limited to, (1) anionic (based on sulfate, sulfonate or carboxylate anions), for example, perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate (SLES)), alkyl benzene sulfonate, soaps, and fatty acid salts; (2) cationic (based on quaternary ammonium cations), for example, cetyl trimethylammonium bromide (CTAB) (also known as hexadecyl trimethyl ammonium bromide), and other alkyltrimethylammonium salts, cetylpyridinium chloride (CPC), polyethoxylated tallow amine (POEA), benzalkonium chloride (BAC), and benzethonium chloride (BZT); and (3) zwitterionic (amphoteric), for example, dodecyl betaine, cocamidopropyl betaine, and coco ampho glycinate.

Exemplary nonionic surfactants include, but are not limited to, alkyl poly(ethylene oxide), alkylphenol poly(ethylene oxide), copolymers of poly(ethylene oxide) and poly (propylene oxide) (commercially known as POLOXAMERS or POLOXAMINES), polyoxyethylene octyl phenyl ether (TRITON X-1(00), alkyl polyglucosides, for example, octyl glucoside and decyl maltoside, fatty alcohols, for example, cetyl alcohol and oleyl alcohol, cocamide MEA, cocamide DEA, and polysorbates (commercially known as TWEEN 20, TWEEN 80), for example, dodecyl dimethylamine oxide.

Exemplary biological surfactants include, but are not limited to, micellular-forming surfactants or surfactants that form micelles in solution, for example, DNA, vesicles, phospholipids, and combinations thereof. In one embodiment, the solution comprises polyethylene glycol at a weight percentage of 1-8 wt %, preferably 2-7 wt %, more preferably 3-6 wt % relative to a total weight of the solution. However, in some embodiments, the solution may comprise polyethylene glycol at a weight percentage less than 1 wt % or greater than 8 wt % relative to a total weight of the solution. The polyethylene glycol may have a weight average molecular weight of 0.2-500 kDa, preferably 1-300 kDa, more preferably 2-100 kDa.

In a preferred embodiment, the surfactant is an ionic surfactant. In a further embodiment, the surfactant is SDS. In one embodiment, the SDS may be present at a concentration of 1-800 mM, preferably 5-400 mM, more preferably 10-100 mM, though in some embodiments, the SDS may be present at a concentration of less than 1 mM or greater than 800 mM.

Preferably the solution comprises water so that it is an aqueous solution. The water may be tap water, distilled water, bidistilled water, deionized water, deionized distilled water, reverse osmosis water, and/or some other water. In one embodiment the water is bidistilled to eliminate trace metals. Preferably the water is bidistilled, deionized, deionized distilled, or reverse osmosis water and at 25° C. has a conductivity at less than 10 $\mu$S·cm$^{-1}$, preferably less than 1 $\mu$S·cm$^{-1}$; a resistivity greater than 0.1 M$\Omega$·cm, preferably greater than 1 M$\Omega$·cm, more preferably greater than 10 M$\Omega$·cm; a total solid concentration less than 5 mg/kg, preferably less than 1 mg/kg; and a total organic carbon concentration less than 1000 $\mu$g/L, preferably less than 200 $\mu$g/L, more preferably less than 50 $\mu$g/L.

In an alternative embodiment, the irradiating may not cause the microcrystal exfoliation, and in some embodiments, this may depend on the solution conditions and on the shape and morphology of the crystal. In one embodiment, the irradiating may cause the isomerization of formula I to formula II without the separation of an outer layer. In another embodiment, the irradiating may cause surface deformation, wrinkling, kneading, cracking, pitting, coiling, dissolution, stretching, bending, flattening, exploding, roughening, or smoothing of the microcrystal. In one related embodiment, where the microcrystal is in the form of a microwire or nanowire having an aspect ratio of 10:1 or greater, or a block having a width smaller than 700 nm, the irradiating may induce the microcrystal to curve or coil in one direction. This may be an effect of the isomerization unevenly changing the density of the microcrystal. In other embodiments, the microcrystal in the form of a microwire or nanowire may exhibit lengthening, curving, coiling, wiggling, bending, twisting, rotating, and/or vibrating. In some embodiments, microcrystals that are thick, for instance, having a smallest dimension of at least 2 $\mu$m or at least 5 $\mu$m may expand, flatten, or stretch.

In one embodiment, the microcrystal in the form of a microwire or nanowire may continually exhibit curving, coiling, wiggling, bending, twisting, rotating, and/or vibrating while under a continuous irradiation. In a further embodiment, the movement may continue indefinitely while under irradiation, creating the appearance of "pseudo-perpetual motion." In one embodiment, the continuous irradiation may involve irradiation with both UV and visible light simultaneously, and may further involve irradiation from opposite sides of the microcrystal.

In an alternative embodiment, the microcrystal may not be in a solution, or may be in a solution free of surfactants. In this embodiment, the irradiating may induce a surface deformation, wrinkling, or kneading without separating an outer layer and exfoliating the microcrystal. FIGS. 8A-8D show an example of a microcrystal being irradiated in a surfactant-free solution.

In other embodiments, the irradiation may interact with formula I in different ways. For instance, the irradiation may lead to photooxidation, photodegradation, isomerization into a form other than formula II (for instance, by isomerization on a different bond), fluorescence, light scattering, light transmittance, or heating by absorption. In alternative embodiments, the irradiation may cause isomerization to transition state structure between formula I and formula II for a measurable period of time. In an alternative embodiment, the isomerization may be caused by a different process, for instance, by heating or by mixing the microcrystal with a compound in an excited state, such as a phosphorescent molecule.

In a further embodiment, the microcrystal is formed by seeding a super saturated solution of dissolved formula I in SDS/1-dodecanol with a crystal of formula I. The crystal of formula I may have a form as previously described for the microcrystal, though in a preferred embodiment, the crystal of formula I has an octahedral form. In other embodiments, the crystal of formula I may be in the form of a rectangular prism. Preferably, the crystal of formula I is smaller than the microcrystal. For instance, the length of the longest dimension of the crystal of formula I may be 1-50%, preferably 5-40% of the length of the longest dimension of the microcrystal.

The super saturated solution of dissolved formula I may comprise water, a surfactant, an alcohol, and/or an acid. In one embodiment, the solution of dissolved formula I may comprise water and a surfactant, but no alcohol and no acid. In another embodiment, the solution of dissolved formula I may comprise water, a surfactant, and an alcohol, but no acid. In another embodiment, microcrystals may form without using a crystal of formula I as a seed. In other embodiments, microcrystals of formula II may be formed by seeding a solution of dissolved formula II with a crystal of formula II. In a related embodiment, a mixed solution of dissolved formula I and II may be seeded with a crystal of formula I and/or a crystal of formula II.

The solution of dissolved formula I may comprise dissolved formula I at a concentration of 50-500 mM, preferably 75-250 mM, more preferably 100-150 mM, though in some embodiments, dissolved formula I may be present at a concentration of less than 50 mM or greater than 500 mM.

Where one or more crystals of formula I are used as seeds in the solution of dissolved formula I, the seeds may be present at a concentration of 0.001 mg/mL-0.02 mg/mL, preferably 0.003-0.01 mg/mL, more preferably 0.005-0.007 mg/mL, though in some embodiments, the seeds may be present at a concentration of less than 0.001 mg/mL or greater than 0.02 mg/mL.

In one embodiment, the water may be any of those previously mentioned. Preferably the water is deionized water.

In one embodiment the surfactant may be any of those previously mentioned. In a preferred embodiment, the surfactant is an ionic surfactant. In a further embodiment, the surfactant is SDS. In one embodiment, the SDS may be present at a concentration of 1-800 mM, preferably 5-400 mM, more preferably 10-100 mM, though in some embodiments, the SDS may be present at a concentration of less than 1 mM or greater than 800 mM.

In one embodiment, the alcohol may be methanol, ethanol, 1-propanol, n-butanol, 1-pentanol, 1-hexanol, 1-heptanol, 1-octanol, 1-nonanol, 1-decanol, undecanol, 1-dodecanol, tridecan-1-ol, 1-tetradecanol, pentadecan-1-ol, cetyl alcohol, heptadecan-1-ol, Stearyl alcohol, nonadecan-1-ol, arachidyl alcohol, heneicosan-1-ol, docosanol, tricosan-1-ol, 1-tetracosanol, pentacosan-1-ol, 1-hexacosanol, 1-heptacosanol, 1-octacosanol, 1-nonacosanol, triacontanol, isobutanol, isoamyl alcohol, 2-methyl-1-butanol, phenethyl alcohol, tryptophyl, isopropanol, 2-butanol, 2-pentanol, 2-hexanol, 2-heptanol, cyclohexanol, 2-octanol, tert-butyl alcohol, tert-amyl alcohol, 2-methyl-2-pentanol, 2-methylhexan-2-ol, 2-methylheptan-2-ol, 3-methyl-3-pentanol, or 3-methyloctan-3-ol. Preferably, the alcohol is a straight chain primary alcohol such as methanol, ethanol, 1-propanol, n-butanol, 1-pentanol, 1-hexanol, 1-heptanol, 1-octanol, 1-nonanol, 1-decanol, undecanol, 1-dodecanol, tridecan-1-ol, or 1-tetradecanol. In a preferred embodiment, the alcohol is 1-dodecanol, which may also be denoted as dodecanol, dodecan-1-ol, lauryl alcohol, $CH_3(CH_2)_{10}CH_2OH$, $C_{12}H_{26}O$, or may be abbreviated herein as 1-$C_{12}OH$. In alternative embodiments, non-alcohol solvents may be used in place of the alcohol, such as acetone, dichloromethane, toluene, or some other solvent. The alcohol may be present at a concentration of 0.1-100 mM, preferably 1-50 mM, more preferably 2-20 mM, though in some embodiments, the alcohol may be present at a concentration of less than 0.1 mM or greater than 100 mM. In one embodiment, the alcohol is not present, and microcrystals may form having octahedral shapes, rather than tetragonal shapes or rectangular shapes.

In one embodiment, the acid may be boric acid, carbonic acid, hydrochloric acid, acetic acid, propionic acid, nitric acid, sulfuric acid, phosphoric acid, acetic acid, or some other acid. Preferably the acid is phosphoric acid. In one embodiment, no acid may be present. However, in embodiments where the acid is present, the acid may be present at a concentration of 1-10 M, preferably 2-8 M, more preferably 3.5-7.5 M. Where the acid is phosphoric acid and is present at a concentration of 5-8 M, elongated microcrystals in the form of microwires or nanowires may form from the seed crystals.

In additional embodiments, other additives may be used to direct the growth or deposition of the microcrystals, such as polyethylene glycol, DMF, or sodium citrate.

For growing or precipitating microcrystals from a solution of dissolved formula I, with or without seed crystals, the solution may be periodically agitated in order to keep the crystals and other components well dispersed and/or dissolved. This agitation may be by shaking, sonicating, rotating, tilting, or stirring. However, in some embodiments, the solution may be agitated only once and then allowed to sit undisturbed. In some embodiments, the solution may be periodically exposed to the air. This air exposure may help certain surfactants, such as SDS, remain dissolved in the solution. Preferably, the solution is also heated during the growth or precipitation of the microcrystals. For instance, the solution may be heated to 35-65° C., preferably 37-62° C., or about 40° C., or about 60° C. In some embodiments, the solution may be heated at a higher temperature, and then heated at a lower temperature. For instance, the solution may initially be heated at about 60° C. and then may be heated at about 40° C. This process of growing or precipitating the microcrystals may be carried out for 30 min-48 h, preferably 1-24 h, more preferably 2-12 h. In one embodiment, at least 80 wt %, preferably at least 90 wt %, more preferably at least 95 wt %, even more preferably at least 98 wt % of the initially dissolved formula I forms microcrystals, relative to a total weight of the initially dissolved formula I. In one embodiment, the microcrystals are washed with water or some other solution before characterizing or subjecting to irradiation.

In a further embodiment, the compound of formula I is produced by irradiating a compound of formula II with light having a visible wavelength. For instance, formula I may be produced by synthesizing or obtaining formula II. Formula II may be dispersed in a solution and then irradiated with visible light, for instance, light having a wavelength of 420-750 nm, preferably 450-700 nm, more preferably 475-650 am. This irradiation may isomerize formula II to formula I. The light may have a power density as that previously mentioned, and the irradiating may be carried out with other parameters as previously mentioned. In a preferred embodiment, the exposure time may be 10 min-3 h, preferably 30 min-2 h, in order to isomerize most of formula II into formula I. For instance, after a period of 2 h of irradiating a solution initially comprising formula II, the irradiated solution may comprise 90-99.95 mol % formula I, preferably 95-99.90 mol % formula I, even more preferably 99-99.5 mol % formula I in relation to the total number of moles of formula I and formula II. In one embodiment, a panel of white LEDs may be used as the light source. In one embodiment, the irradiating may be carried out at an elevated temperature, for instance, 30-65° C. or 40-60° C. In another embodiment, formula I may be produce by heating a compound of formula II without irradiation.

In one embodiment, a plurality of microcrystals are formed by seeding or by otherwise precipitating from a solution of formula I, using conditions described previously or using different conditions. The microcrystals formed may be monodisperse, having a coefficient of variation or relative standard deviation, expressed as a percentage and defined as the ratio of the microcrystal length or width standard deviation ($\sigma$) to the mean length or width ($\mu$), respectively, multiplied by 100%, of less than 25%, preferably less than 10%, preferably less than 8%, preferably less than 6%, preferably less than 5%. In a preferred embodiment, the microcrystals have a monodisperse width distribution ranging from 80% of the average width to 120% of the average width, preferably 85-115%, preferably 90-110% of the average width. In another embodiment, the microcrystals may be monodisperse in width wherein 70-99%, preferably 80-97% of the microcrystals have a width in the range of 0.8-1.2 m. In another embodiment, the microcrystals may be considered monodisperse in width, but not length.

In one embodiment, the method also involves the step of irradiating the exfoliated microcrystal with light having a wavelength of 220-750 nm to produce a second exfoliated microcrystal and a second layer having a thickness of 200-600 nm. In one embodiment, this additional irradiating step may be with light having the same wavelength as described previously, for example, 220-420 nm, preferably 250-410 nm, more preferably 300-405 nm.

In another embodiment, the light may have a wavelength of 420-750 nm, preferably 450-700 nm, more preferably 475-650 nm. In this embodiment, light having a wavelength of 420-750 nm may induce an isomerization of formula II to formula I. Here, the formula II may be in the exfoliated microcrystal, the separated outer layer, or both. This irradiation with light having a wavelength of 420-750 nm may create the separation of another outer layer, or may deform a part of the exfoliated microcrystal, and/or may deform the existing outer layer.

In one embodiment, one or more microcrystals may produce a plurality of outer layers or nanopeels that have a monodisperse thickness. Here, the thicknesses of the outer layers or nanopeels, having a coefficient of variation or relative standard deviation, expressed as a percentage and defined as the ratio of the standard deviation ($\sigma$) thickness to the mean ($\mu$) thickness, respectively, multiplied by 100%, of less than 25%, preferably less than 10%, preferably less than 8%, preferably less than 6%, preferably less than 5%. In a further embodiment, the outer layers or nanopeels may have a monodisperse thickness, and 70-99%, preferably 75-95% of the outer layers or nanopeels may have a thickness within the range of 300-500 nm, preferably 320-480 nm.

In one embodiment, the microcrystal is on an exterior surface of an object. In this embodiment, the exfoliation of the microcrystal may enable the exterior surface to self-renew, for instance, against weathering or other damage. In one embodiment, the microcrystal may be embedded in a resin or varnish on the exterior surface. In one embodiment, a surface for cell culture (for instance, growing adhesive cells), may be coated with a compound comprising the microcrystal. In this embodiment, a pulse of light may be used to initiate exfoliation of the microcrystal and detach the cells from surface.

In one embodiment, the microcrystal is a component of an implant or orthopedic device. Preferably, the implant or orthopedic device is intended for temporary use, with a structural integrity dependent on the microcrystal. For example, the implant or orthopedic device may be a cast. When the implant or orthopedic device is no longer needed, it may be irradiated with light to induce exfoliation of the microcrystal, significantly reducing the strength of the implant or orthopedic device and allowing it to be more easily removed.

In one embodiment, the microcrystal is a component of a photosensitive switch. In this embodiment, the microcrystal is incorporated in such a way that its isomerization breaks an existing circuit and/or creates a new circuit. In one embodiment, exposure to visible light, or intense visible light such as sunlight, may induce the isomerization from formula I to formula II. The photosensitive switch may trigger a circuit linked to an indicator light, an auditory alarm, a thermostat, an electric motor, a data recorder, a radio transmitter, or some other device.

In one embodiment, the microcrystal is a component of a composition that comprises a dye or a pigment. The dye or pigment may be an azin dye, an azo dye, a diarylmethane dye, a fluorescent dye, a food coloring, a fuel dye, an ikat dye, an indigo structured dyean, a solvent, indophenol dye, a perylene dye, a phenol dye, a quinoline dye, a rhodamine dye dye, a staining dye, a thiazine dye, a thiazole dye, a triarylmethane dye, a vat dye, a violanthrone dye, a metal-based pigment, or some other type of dye or pigment. In one embodiment, the dye or pigment may help deliver irradiation to the microcrystal, for instance, by light scattering or by absorbing light of specific frequencies. In another embodiment, the composition may be used in a visual display, such as artwork or an advertisement, in which light irradiation degrades an outer coating of the composition and reveals a surface underneath.

In another embodiment, the microcrystal may be a component of a composition used to encapsulate a compound for a photo-triggered delayed release. Examples of this compound include, but are not limited to, a dye, a drug, a fertilizer, a detergent, or a reactant.

In one embodiment, the microcrystal is a component of an adhesive. The adhesive may be a thermoplastic (hot-melt) rubber resin adhesive, a solvent-based resin adhesive, a polyphenol resin, an epoxy, a silicone based adhesive, a polyvinyl acetate based adhesive, a polyurethane based adhesive, a thermoplastic or thermosetting plastic, or an acrylic polymer based adhesive. Preferably, the adhesive may comprise an acrylic polymer based adhesive or resin, such as polymers formed from methacrylate, cyanoacrylate, methyl methacrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA) monomers, or mixtures thereof. The microcrystal may be present in the adhesive at a weight percent of 0.1-50 wt %, preferably 2-25 wt %, more preferably 5-50 wt % relative to a total weight of the adhesive. However, in some embodiments, the adhesive may comprise less than 0.1 wt % or more than 50 wt % microcrystal. The adhesive may be doped with other compounds such as phthalic anhydride, poly(methyl methacrylate), hydroquinone, or sulfonic acid in order to adjust physical and chemical properties such as viscosity, curing speed, or adhesion strength. These other compounds may be doped at a weight percent of 0.01-10 wt %, preferably 0.1-5.0 wt %, more preferably 0.2-3.0 wt % relative to a total weight percentage of the adhesive. It is envisioned that irradiation may induce exfoliation of the microcrystal, and weaken the adhesive to enable its removal or separation.

In further embodiments, it is envisioned that the microcrystal may be used in other applications relating to self-renewing surfaces, self-cleaning surfaces, self-repairing surfaces, photo-active compositions, and temporary structures. In one embodiment, the microcrystal may adsorb contaminants or other substances from liquid or gas phase. Following irradiation and exfoliation, an exfoliated microcrystal exposes a fresh surface for continued adsorption. In other embodiments, due to the optical control of the isomerization, formula I or formula II may be used as a template for synthesizing organic compounds of specific a stereochemistry.

Referring now to the drawings, wherein like reference numerals designate identical or corresponding parts throughout the several views:

FIG. 1 is a schematic of making cis-DMAAM μ-log (seeds) and larger cis-DMAAM μ-logs. By route "a," cis-DMAAM μ-logs (seeds) may be formed by adding a solution of cis-DMAAM in DMF (ca. 0.13 molar) to a solution of SDS/1-dodecanol set at 40° C. while stirring at 1,500 rpm. To make larger cis-DMAAM μ-logs, seeds produced by route "a" may be added as seeds to a saturated solution of cis-DMAAM in SDS/1-dodecanol (route "b").

Figure 2A:
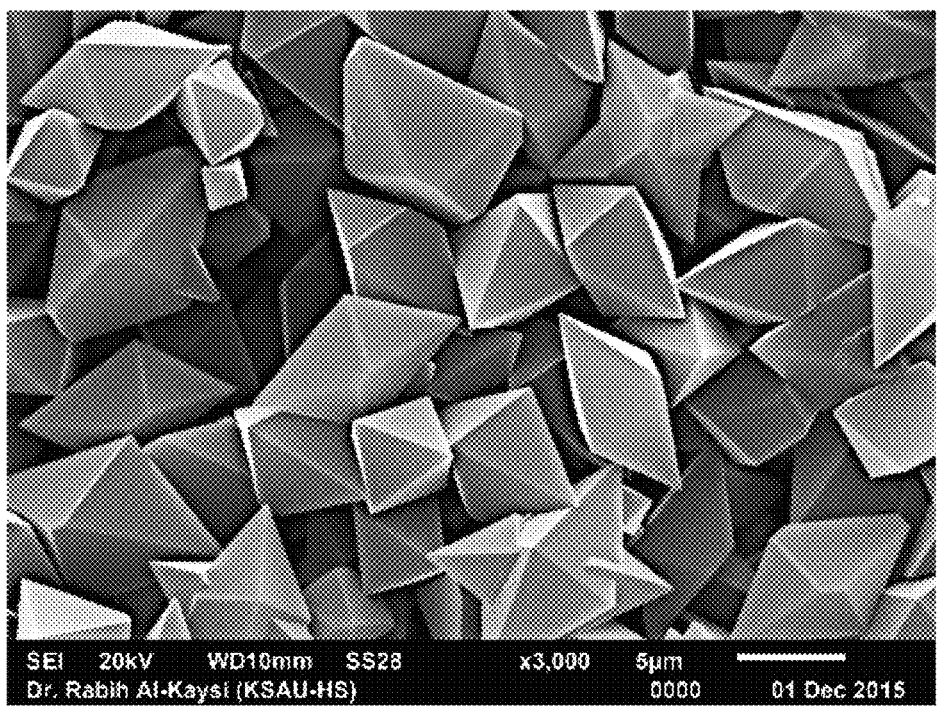
FIG. 2A shows an SEM image of octahedral cis-DMAAM microcrystals formed in 0.02 M SDS without 1-dodecanol and without phosphoric acid.
Figure 2B:
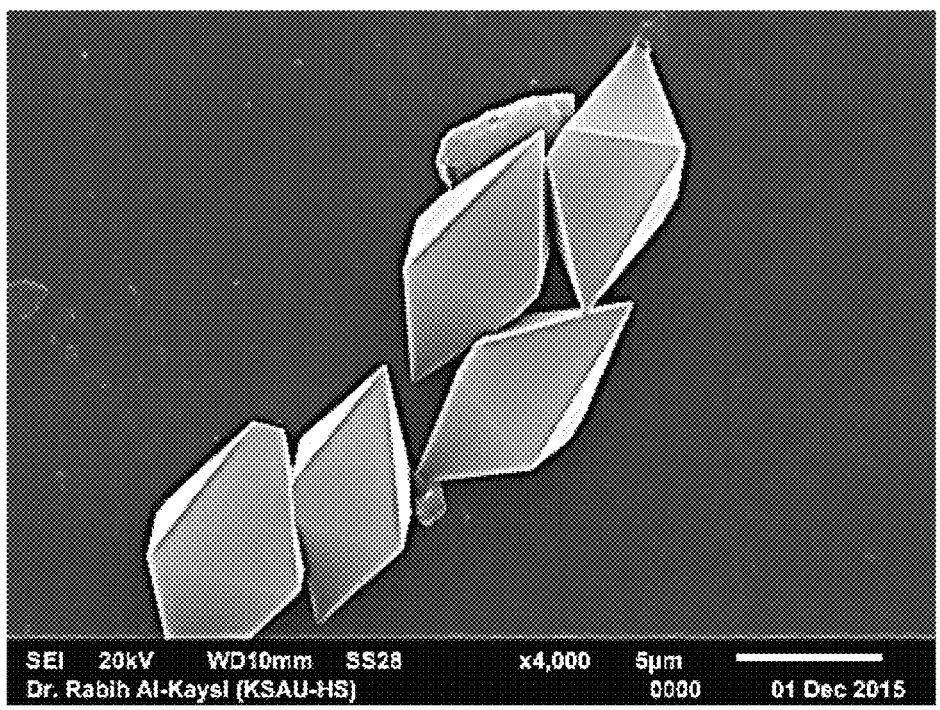
FIG. 2B shows another SEM image of octahedral cis-DMAAM microcrystals formed by the same conditions as in FIG. 2A.
Figure 2C:
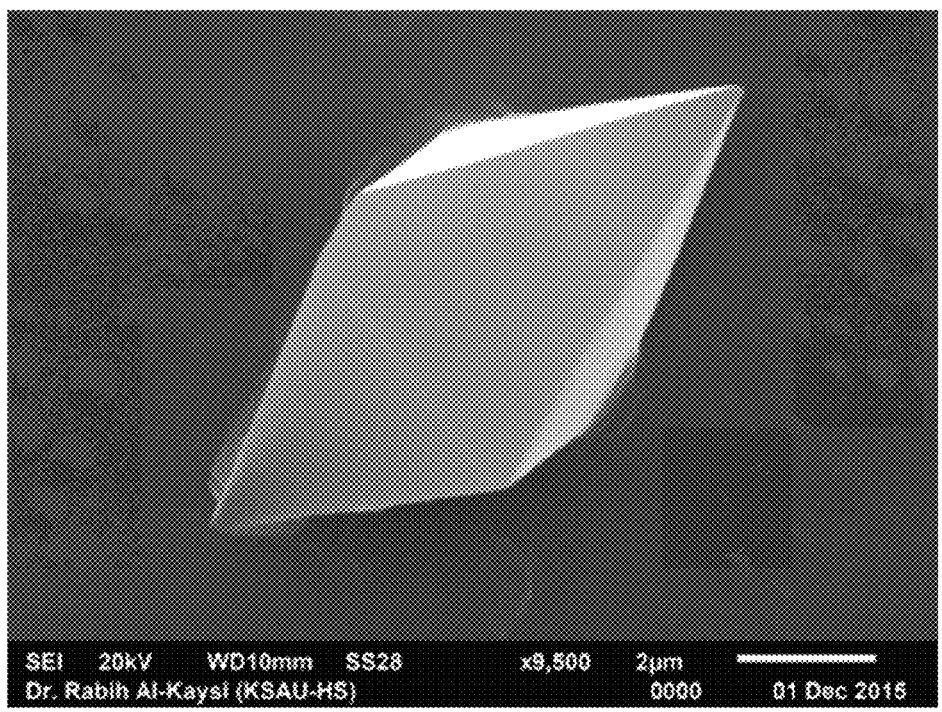
FIG. 2C shows another SEM image of octahedral cis-DMAAM microcrystals formed by the same conditions as in FIG. 2A.

FIGS. 2A-2C show SEM images of octahedral cis-DMAAM microcrystals formed by precipitation from 0.02 M SDS without 1-dodecanol and without phosphoric acid. This procedure is similar to the scheme in FIG. 1.

Figure 2D:
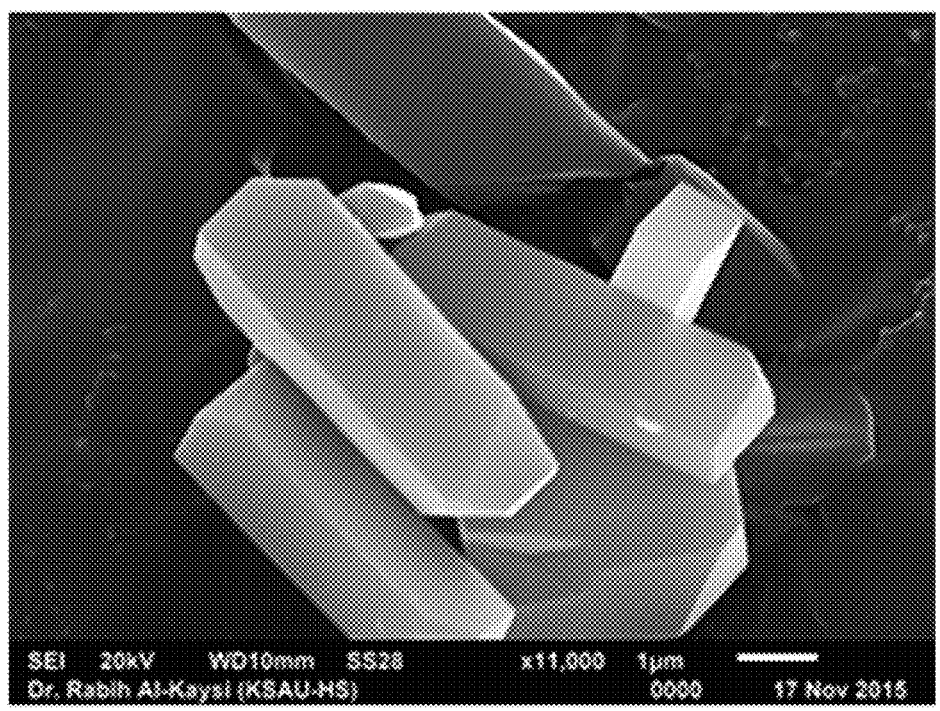
FIG. 2D shows an SEM image of faceted µ-blocks formed in 0.02 M SDS and 0.88 mM 1-dodecanol, without phosphoric acid
Figure 2E:
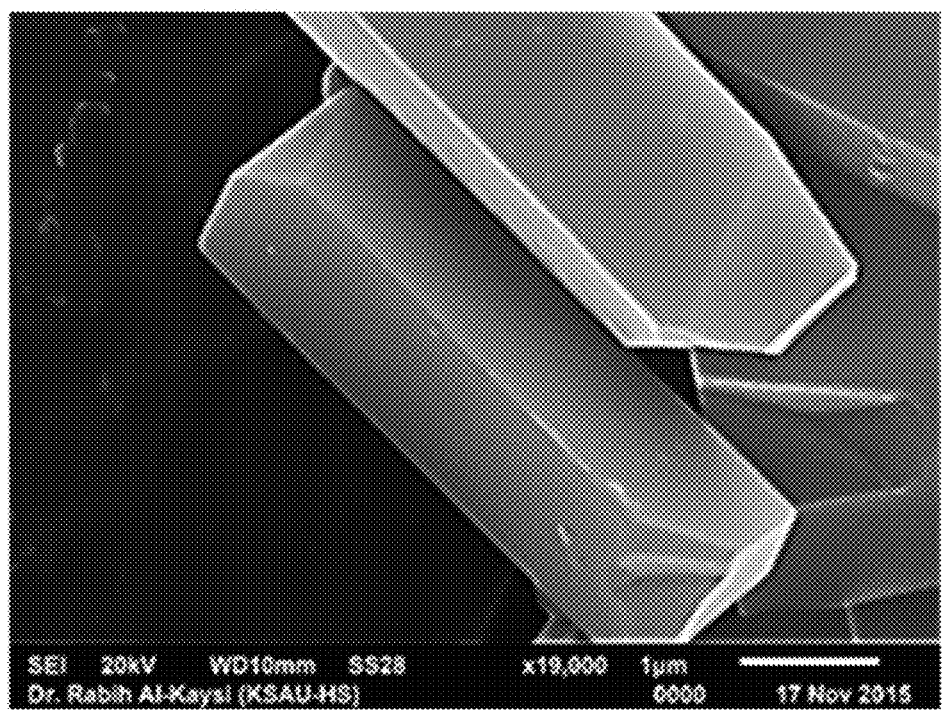
FIG. 2E shows another SEM image of faceted µ-blocks formed by the same conditions as in FIG. 2D.
Figure 2F:
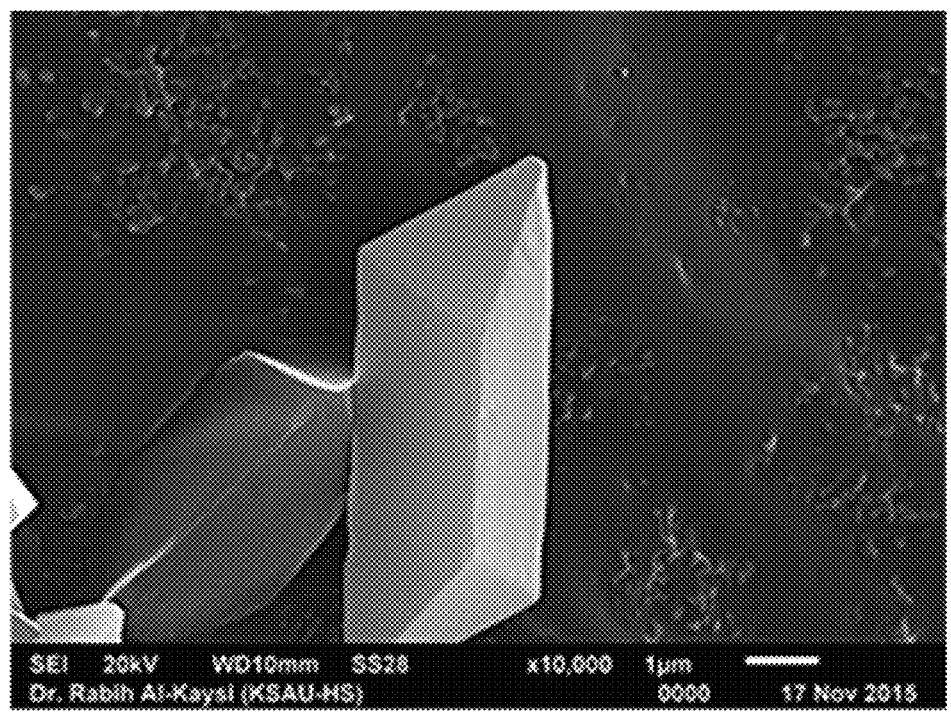
FIG. 2F shows another SEM image of faceted µ-blocks formed by the same conditions as in FIG. 2D.

FIGS. 2D-2F show SEM images of faceted microblocks (μ-blocks) formed by increasing the molar ratio of 1-dodecanol to SDS 4% to inhibit face growth. Here, the solution comprises 0.02 M SDS, 0.88 mM 1-dodecanol, and no phosphoric acid.

Figure 2G:
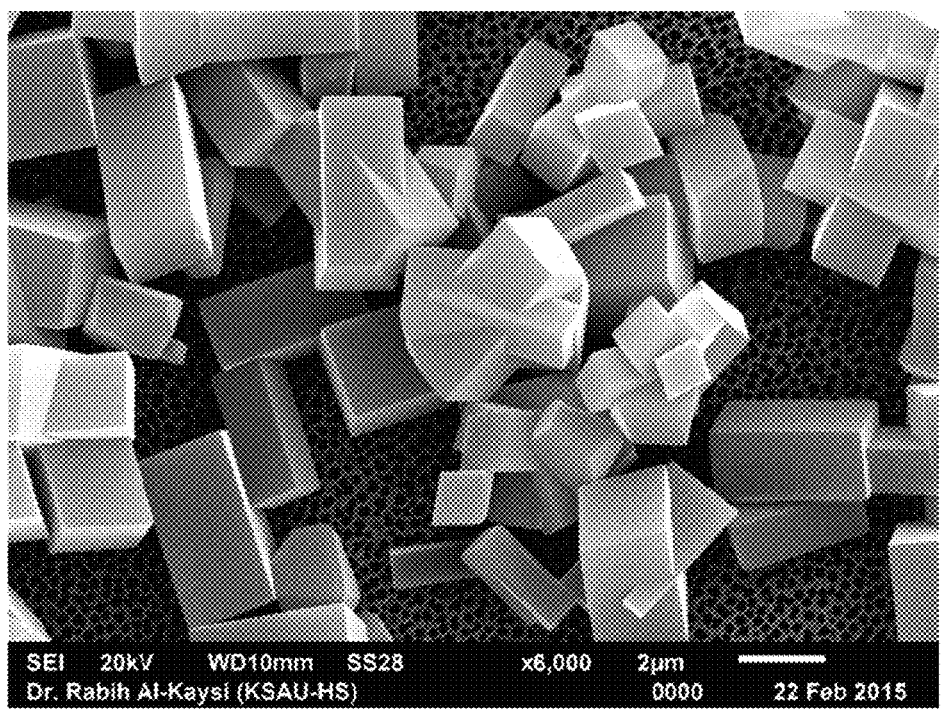
FIG. 2G shows an SEM image of µ-blocks formed in 0.01 M SDS and 0.002 M 1-dodecanol, without phosphoric acid and under continuous stirring via a magnetic stirrer.
Figure 2H:
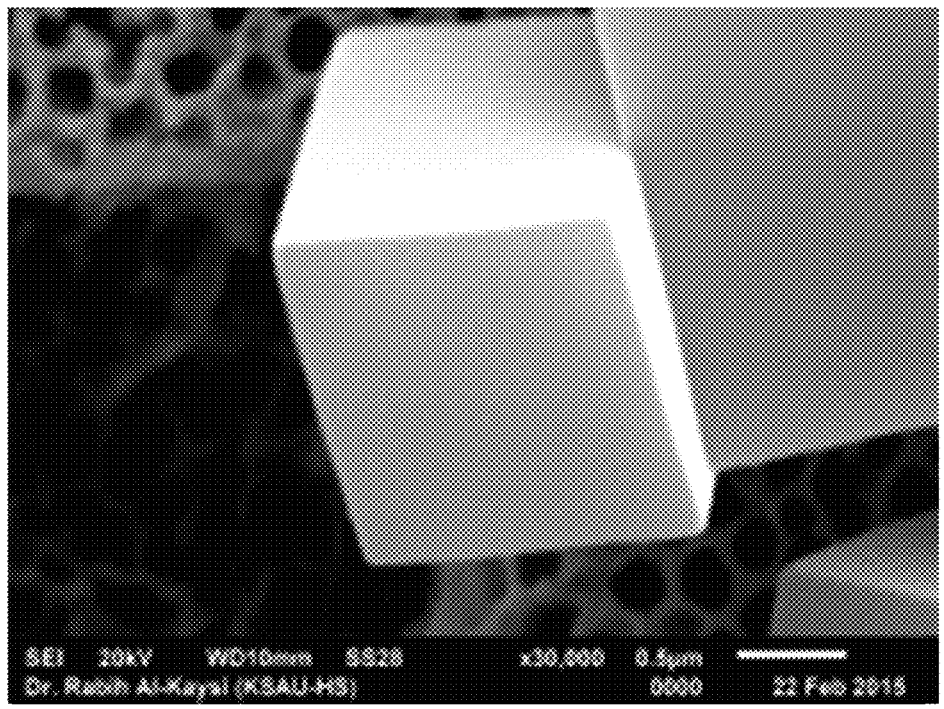
FIG. 2H shows another SEM image (zoomed in) of µ-blocks formed by the same conditions as in FIG. 2G.
Figure 2I:
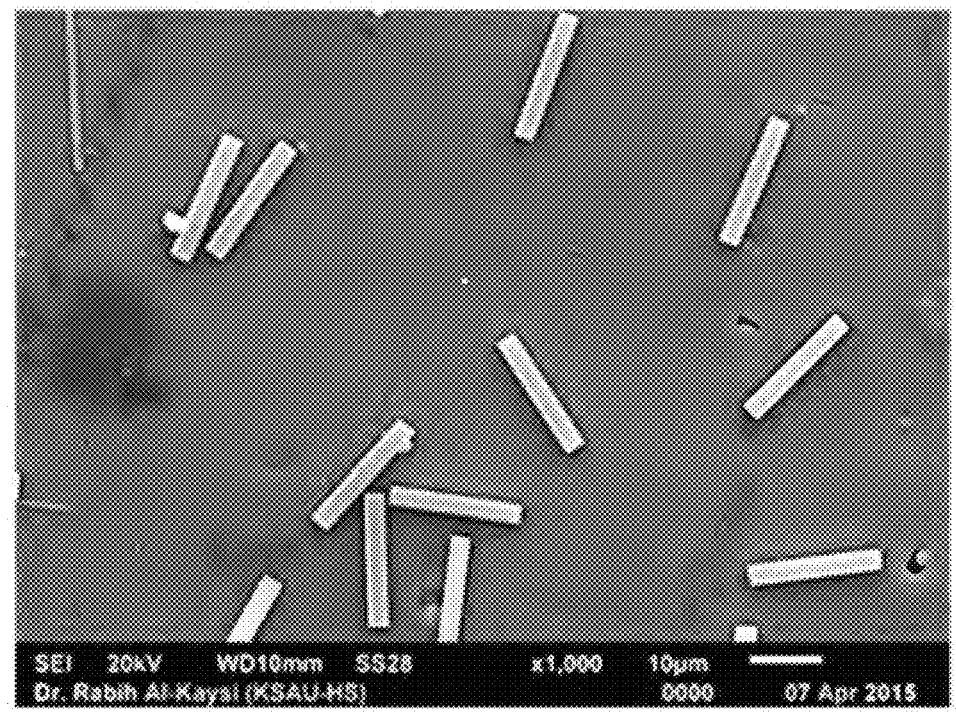
FIG. 2I shows an SEM image of larger t-blocks formed by introducing seed crystal from FIG. 2G to a supersaturated solution of cis-DMAAM in 0.01 M SDS and 0.002 M 1-dodecanol then left undisturbed at 40° C. for 24 hours.
Figure 2J:
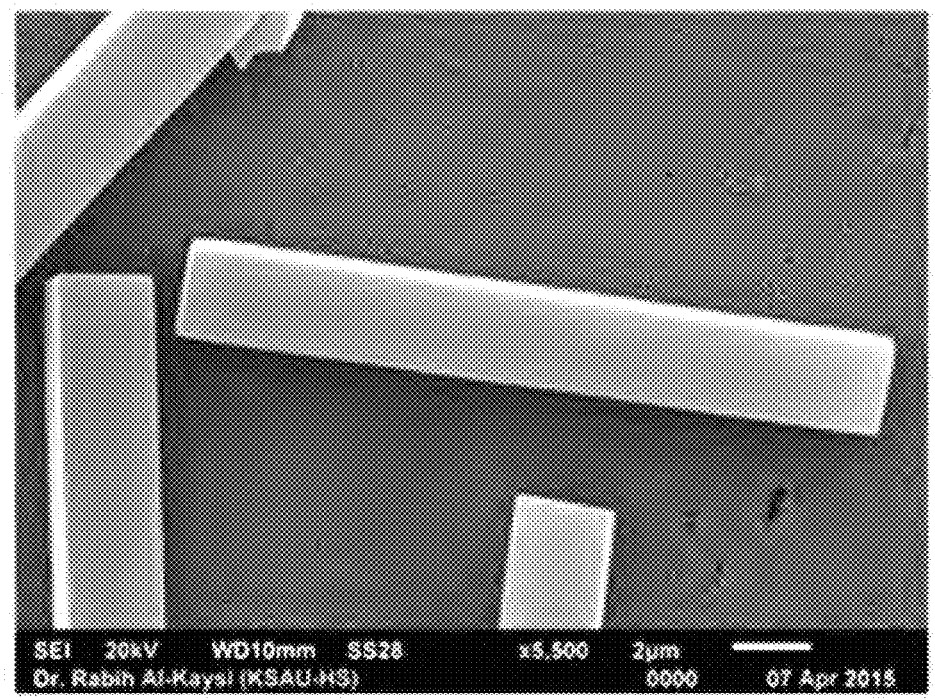
FIG. 2J shows another SEM image of µ-blocks formed by the same conditions as in FIG. 2I.

FIGS. 2G-2J show SEM images of μ-blocks formed in 0.01 M SDS and 0.002 M 1-dodecanol, without phosphoric acid. FIG. 2G SEM image of seed cis-DMAAM prepared using route "a" from FIG. 1. FIG. 2H is a zoomed in image of FIG. 2G. FIG. 2I is an SEM image of larger cis-DMAAM μ-blocks prepared following route "b" from FIG. 1. FIG. 2J is a zoomed in image of FIG. 2I.

Figure 2K:
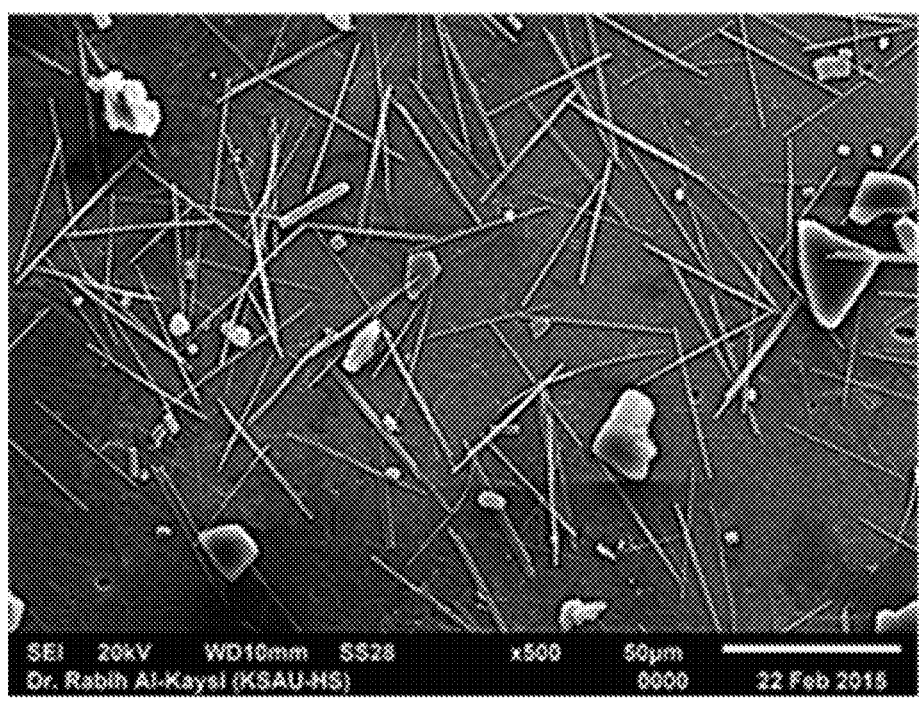
FIG. 2K shows an SEM image of microwires formed in 0.01 M SDS, 0.002 M 1-dodecanol, and 7 M phosphoric acid.
Figure 2L:
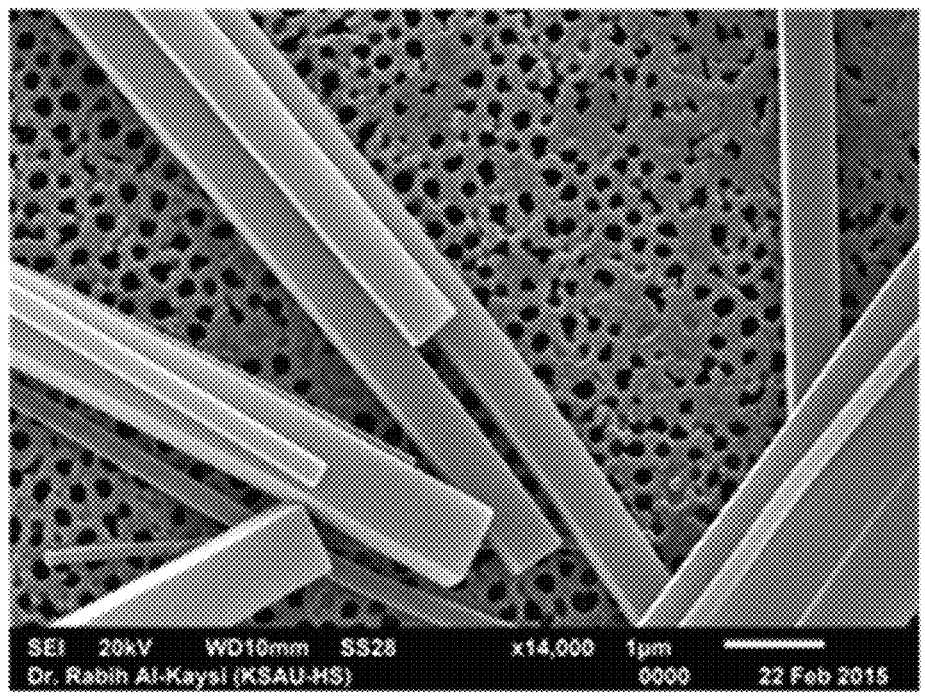
FIG. 2L shows another SEM image of microwires formed by the same conditions as in FIG. 2K.
Figure 2M:
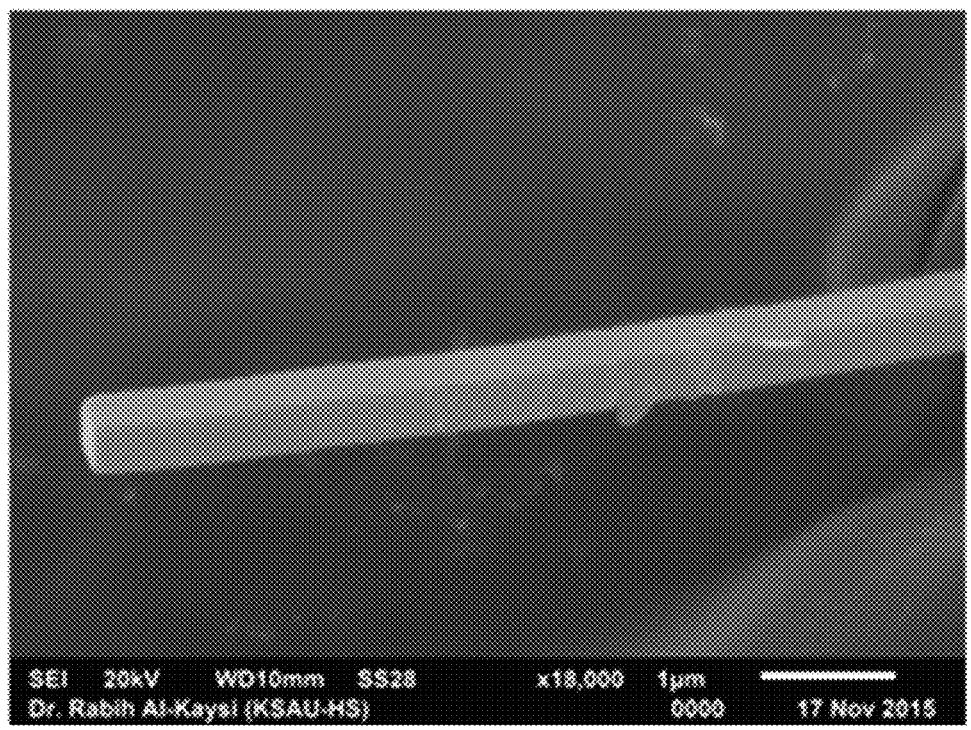
FIG. 2M shows another SEM image of microwires formed by the same conditions as in FIG. 2K.

FIGS. 2K-2M show SEM images of microwires formed in 0.01 M SDS, 0.002 M 1-dodecanol, and 7 M phosphoric acid. The mixture was tumble rotated.

Figure 3A:
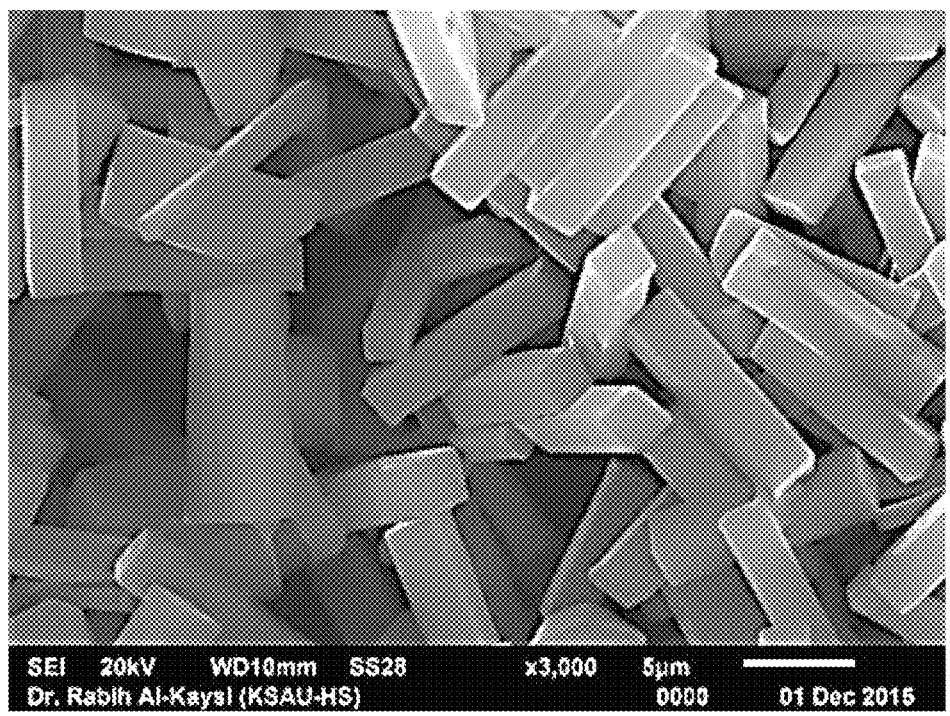
FIG. 3A shows an SEM image of large cis-DMAAM µ-blocks formed in 0.01 M SDS, 0.033 M 1-dodecanol, and 3.5 M phosphoric acid with stirring.
Figure 3B:
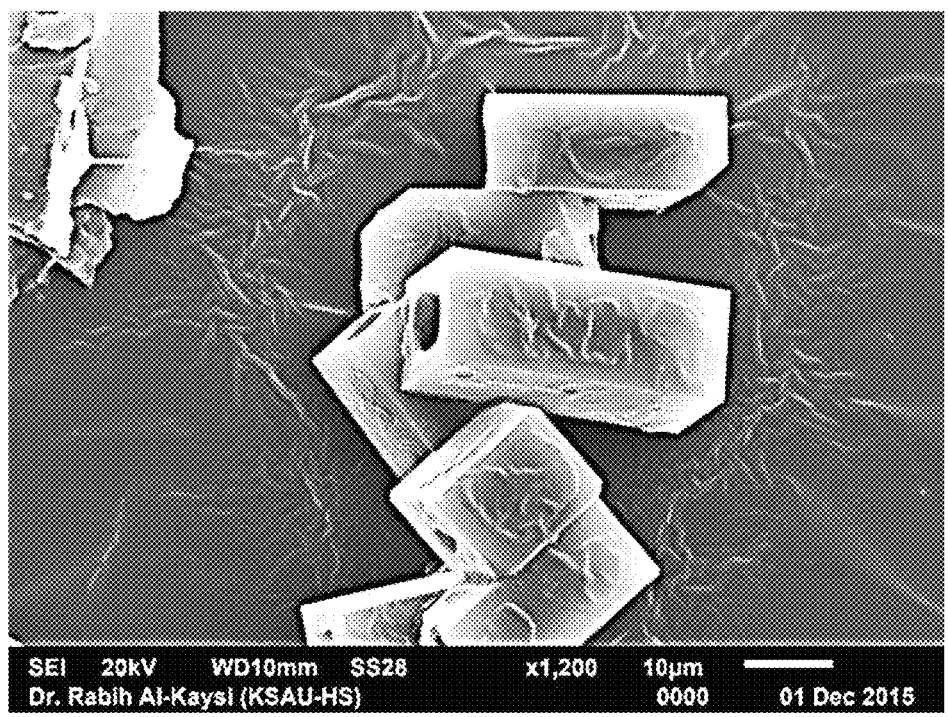
FIG. 3B shows an SEM image of large cis-DMAAM µ-blocks formed by the same conditions as in FIG. 3A, but without stirring.
Figure 3C:
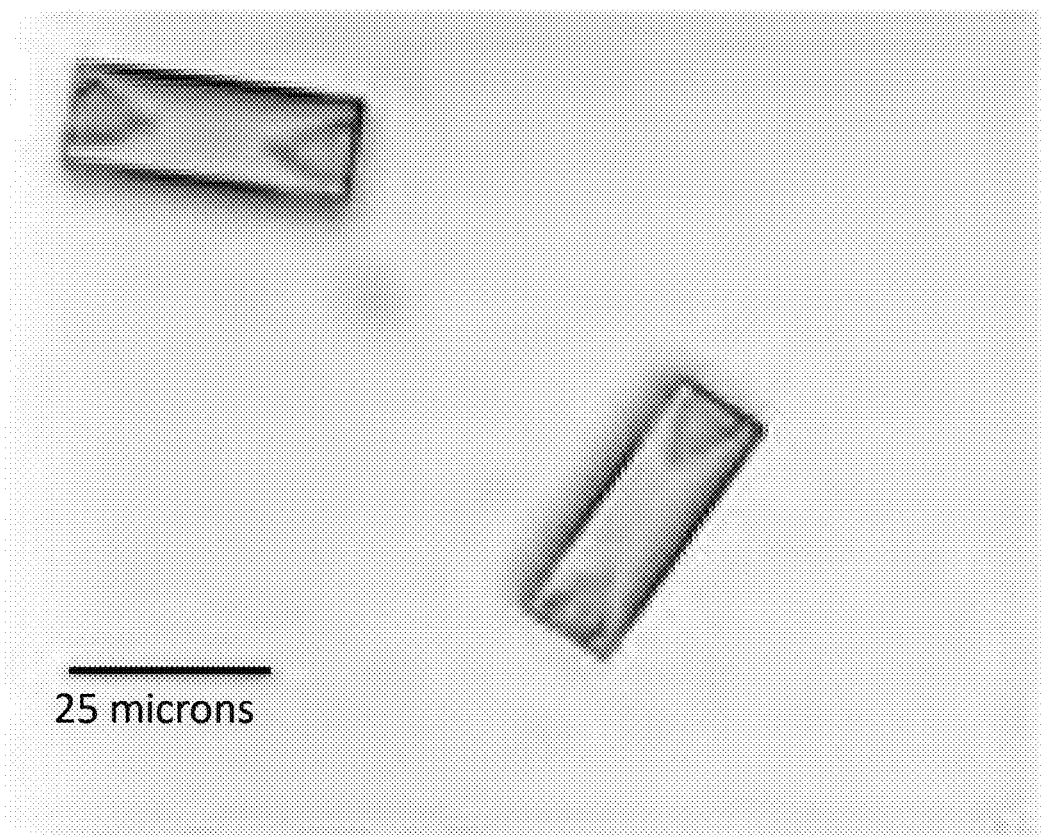
FIG. 3C is an optical microscopy image of the sample in FIG. 3B, scale bar 25 µm.

FIGS. 3A-3B show SEM images of large cis-DMAAM μ-blocks formed in 0.01 M SDS, 0.033 M 1-dodecanol, and 3.5 M phosphoric acid. FIG. 3A is stirred during the μ-block formation. FIG. 3B is not stirred during the μ-block formation, and the μ-blocks have holes on either end as a result of not stirring. FIG. 3C is an optical microscopy image of the sample in FIG. 3B, scale bar 25 μm.

Figure 4A:
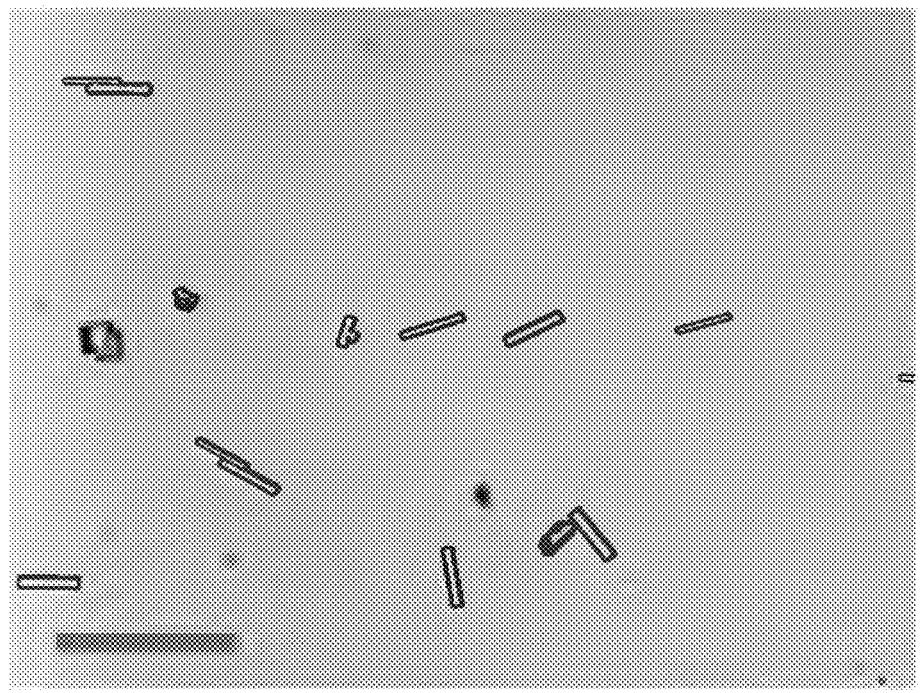
FIG. 4A is an optical microscopy image of µ-logs grown from seeds.
Figure 4B:
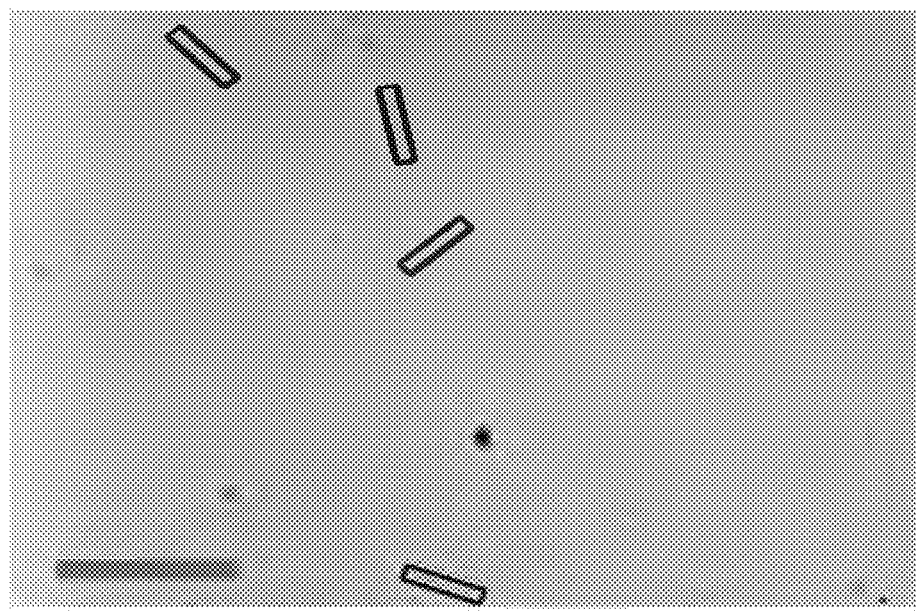
FIG. 4B is another optical microscopy image of µ-logs grown from seeds.
Figure 4C:
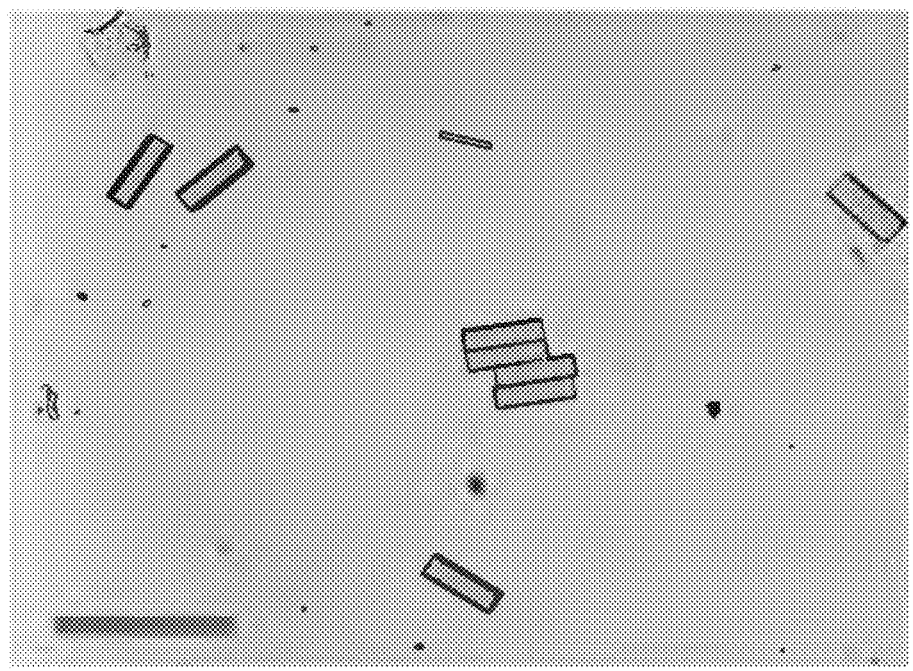
FIG. 4C is another optical microscopy image of µ-logs grown from seeds.
Figure 4D:
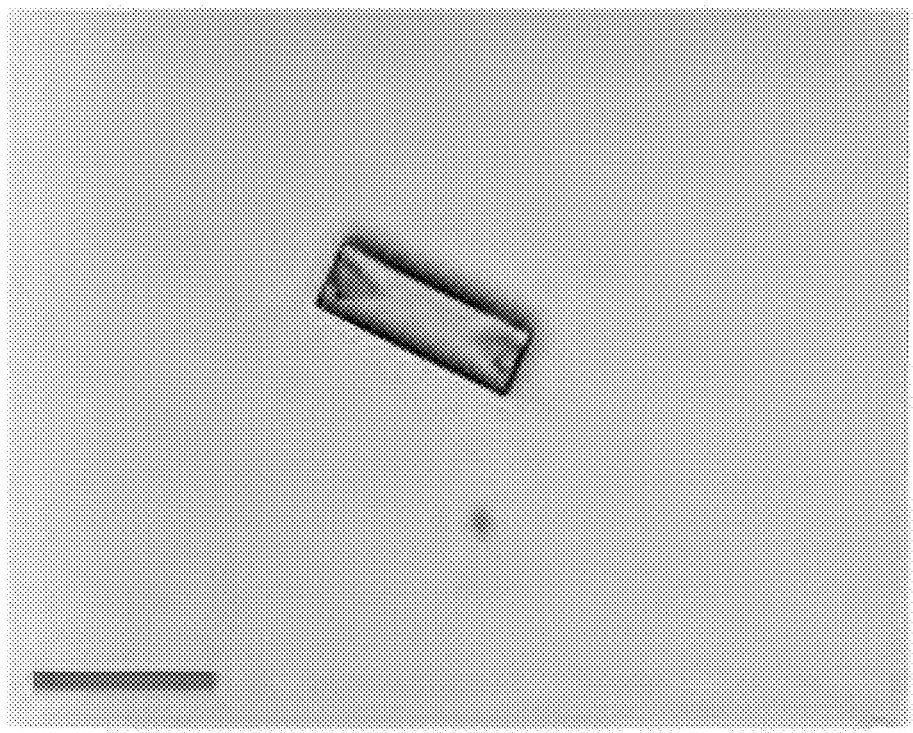
FIG. 4D is an optical microscopy image of µ-logs grown without seeds.
Figure 4E:
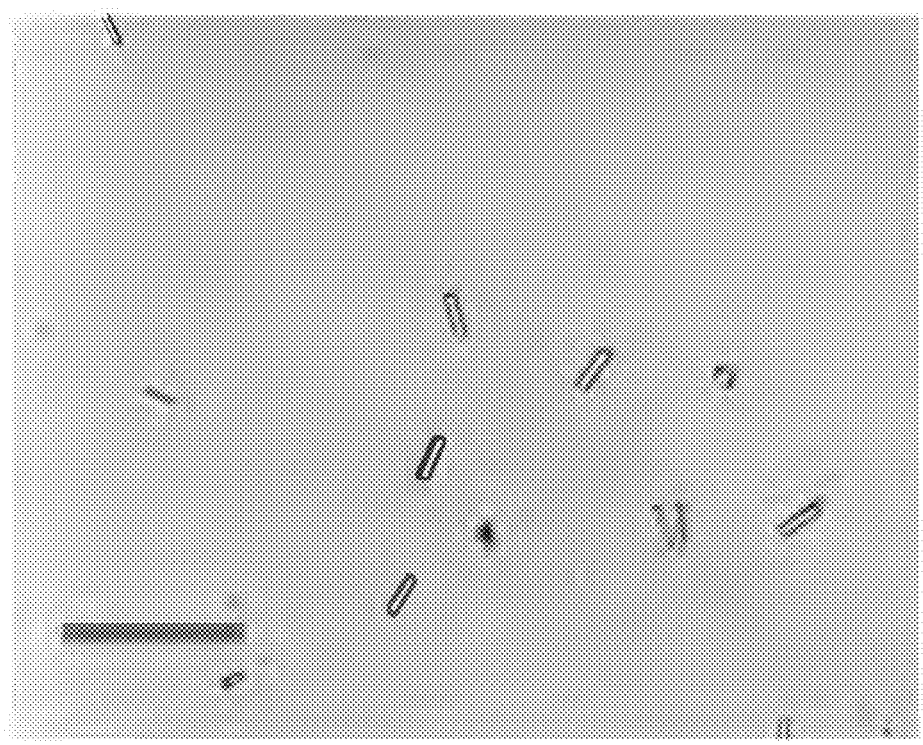
FIG. 4E is an optical microscopy image of the seeds used in FIGS. 4A-4C.

FIGS. 4A-4D show different μ-log sizes grown from different amounts of seeds of FIG. 4E:

In FIG. 4A, micrologs of length≈8.5 μm and width≈1.5 μm are formed by adding 500 μL seed suspension (0.001 mg seeds) to a saturated solution of cis-DMAAM in SDS/1-dodecanol and tumble-rotating the mixture. Scale bar is 25 μm.

In FIG. 4B, micrologs of length≈12 μm and width≈3 μm are formed by adding 50 μL seed suspension (0.0001 mg seeds) to an equivalent saturated solution of cis-DMAAM in SDS/1-dodecanol and tumble-rotating the mixture. Scale bar is 25 μm.

In FIG. 4C, micrologs of length≈12.5 μm and width≈4.5 μm are formed by adding 25 μL seed suspension (0.00005 mg seeds) to saturated solution of cis-DMAAM in SDS/1-dodecanol and tumble-rotating the mixture. Scale bar is 25 μm.

In FIG. 4D, no seed suspension is added. Scale bar is 25 μm.

An image of the seeds (length≈5 μm, width≈1 μm) is shown in FIG. 4E. The seeds were prepared following route "a" in FIG. 1. Scale bar is 25 μm.

Figure 5A:
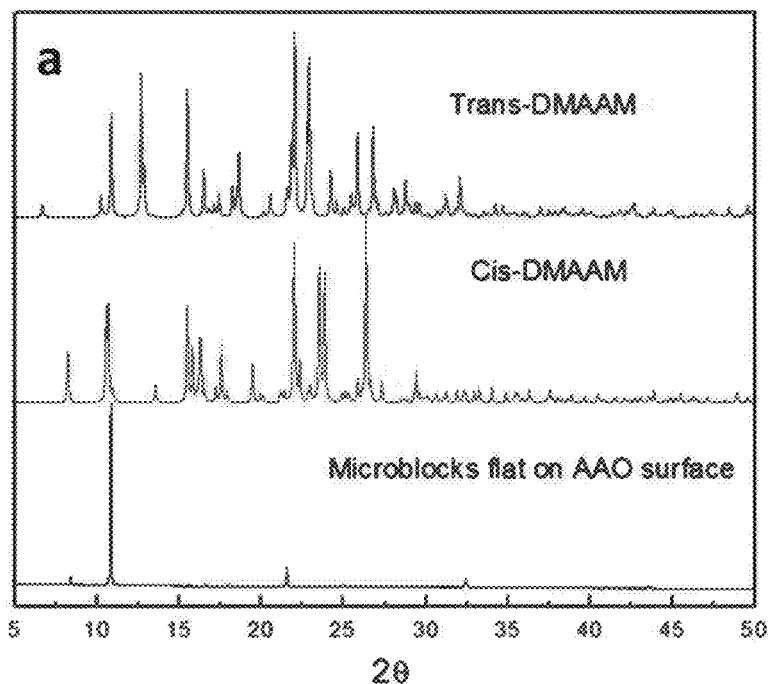
FIG. 5A shows calculated powder X-ray diffraction (PXRD) patterns of trans-DMAAM and cis-DMAAM, and an obtained PXRD pattern of cis-DMAAM µ-blocks.
Figure 5B:
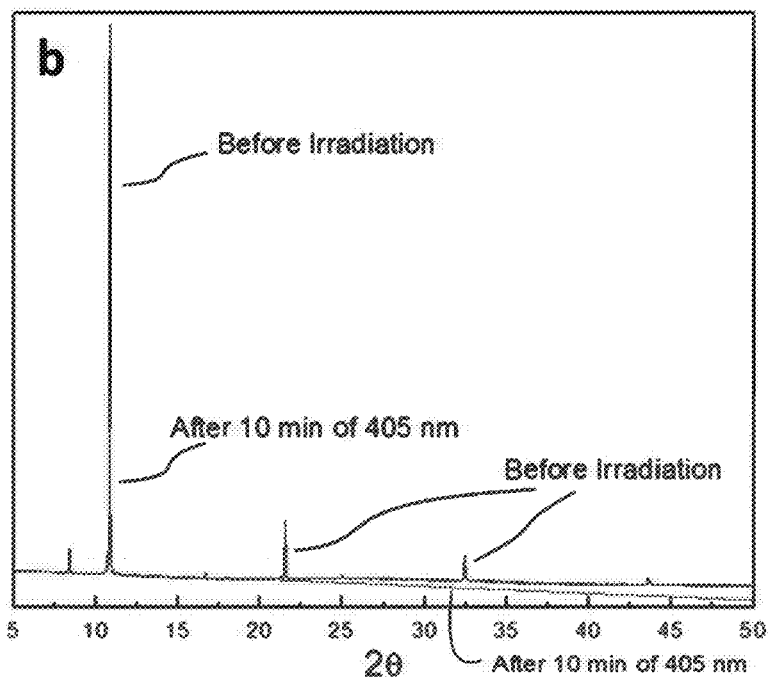
FIG. 5B shows obtained PXRD patterns of cis-DMAAM µ-blocks before and after UV irradiation.
Figure 6A:
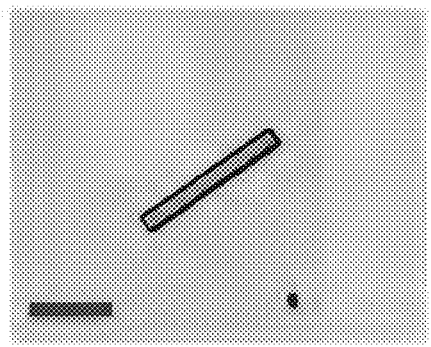
FIG. 6A is an optical microscopy image of a crystal block before a pulse of UV irradiation (365 nm).
Figure 6B:
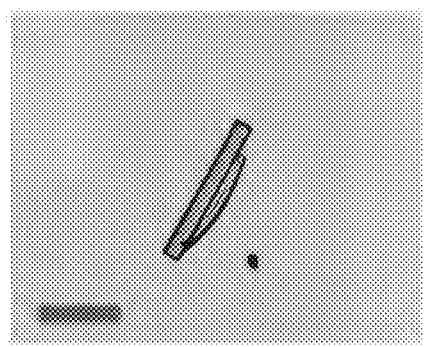
FIG. 6B is the crystal block of FIG. 6A after 15-20 second time period.
Figure 6C:
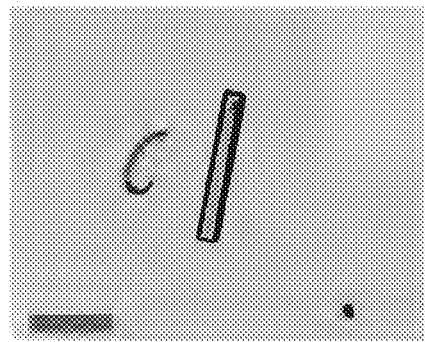
FIG. 6C is the crystal block of FIG. 6B after another pulse of UV light and 15-20 second time period.
Figure 6D:
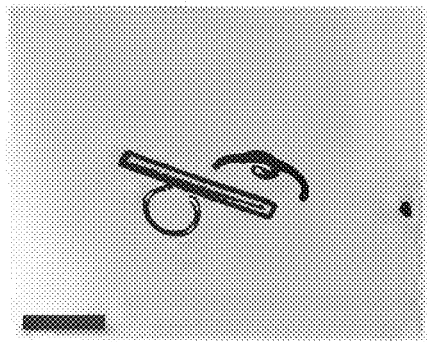
FIG. 6D is the crystal block of FIG. 6C after another pulse of UV light and 15-20 second time period.

FIGS. 5A and 5B show powder X-ray diffraction (PXRD) patterns. FIG. 5A shows calculated PXRD patterns of trans-DMAAM and cis-DMAAM. The obtained PXRD pattern of cis-DMAAM microblocks lying flat on an AAO surface is also shown. FIG. 5B shows the PXRD pattern obtained from cis-DMAAM microblocks lying flat on the AAO surface before and after 10 minutes of 405 nm irradiation.

FIGS. 6A-6D show optical microscopy images of the peel sequence. A crystal block (FIG. 6A) is first exposed to a flash of 405 nm light from a 100 W medium pressure Hg lamp (100 mW/cm$^2$) for a duration of 1 s. Scale bar is 5 μm.

Figure 7A:
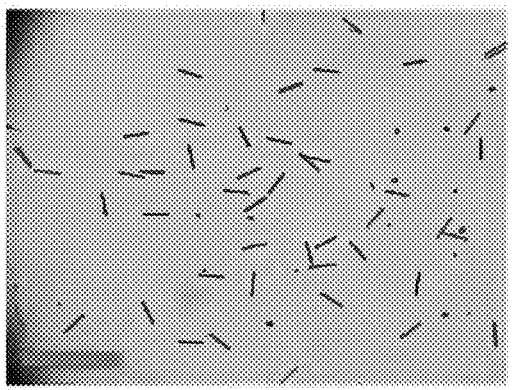
FIG. 7A is a zoomed-out optical microscopy image of crystal blocks before UV irradiation.
Figure 7B:
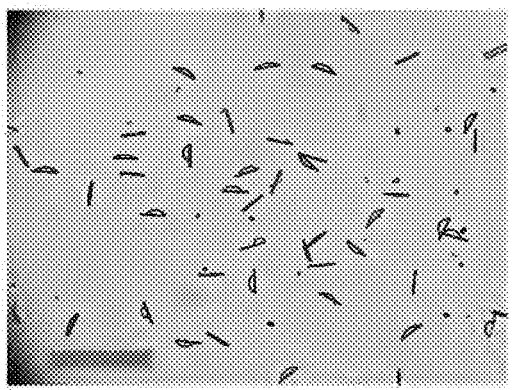
FIG. 7B shows the crystal blocks of FIG. 7A after a time period.
Figure 7C:
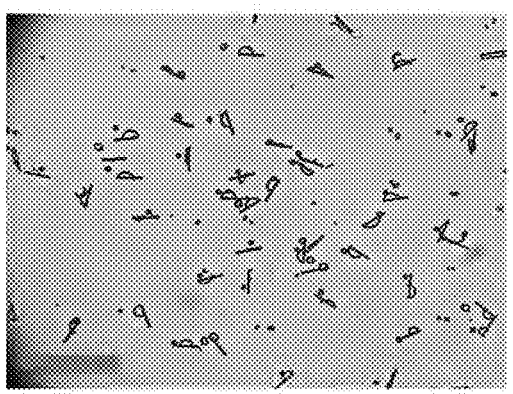
FIG. 7C shows the crystal blocks of FIG. 7B after another time period.
Figure 7D:
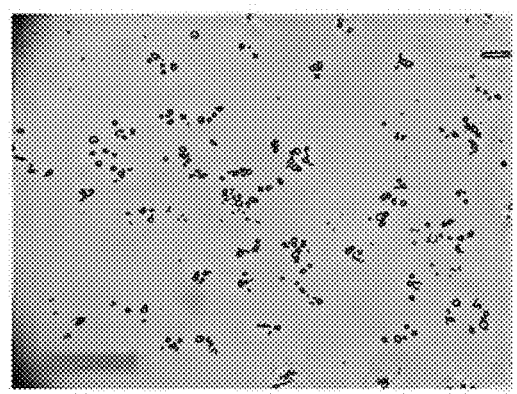
FIG. 7D shows the crystal blocks of FIG. 7C after another time period.
Figure 8A:
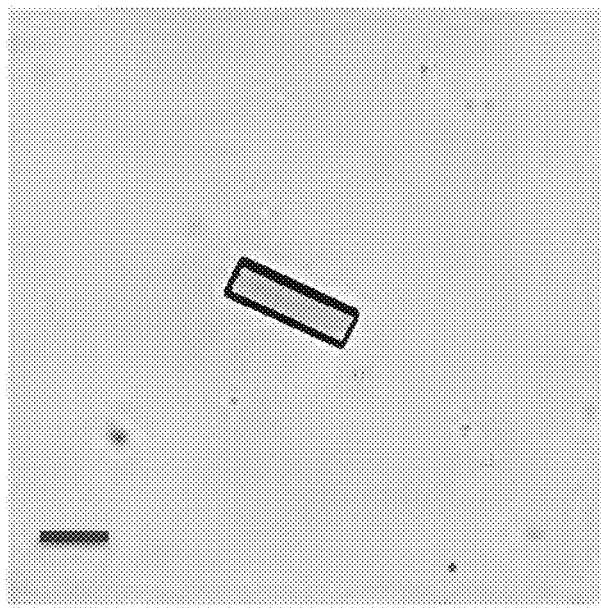
FIG. 8A shows an optical microscopy image of a 13 µm-thick microblock before irradiation and suspended in water without the presence of surfactant.
Figure 8B:
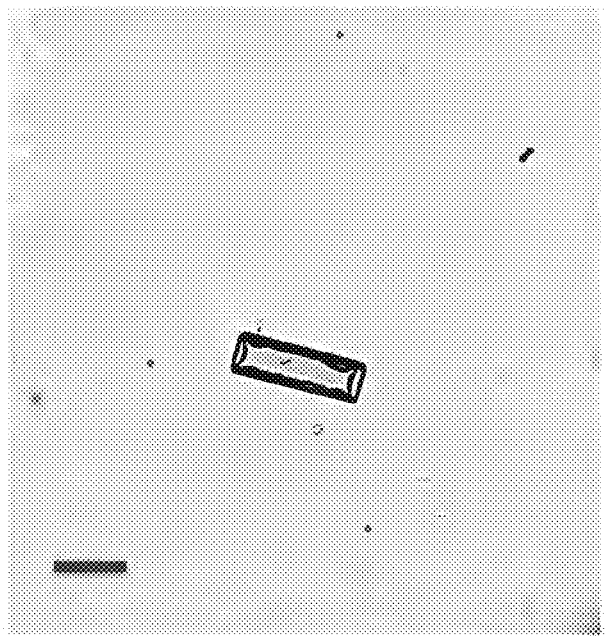
FIG. 8B shows an optical microscopy image of the microblock of FIG. 8B, after a pulse of irradiation with 365 nm light, where due to the lack of surfactant the peel stuck on the surface and did not detach.
Figure 8C:
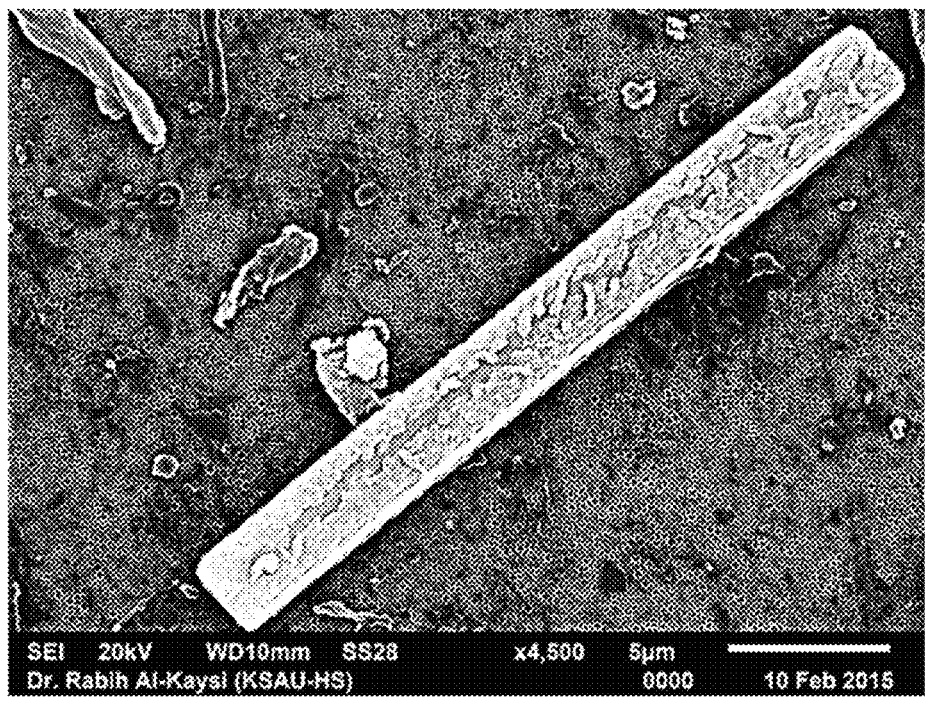
FIG. 8C shows an SEM image of a 13 µm-thick microblock after irradiation without the presence of surfactant.
Figure 8D:
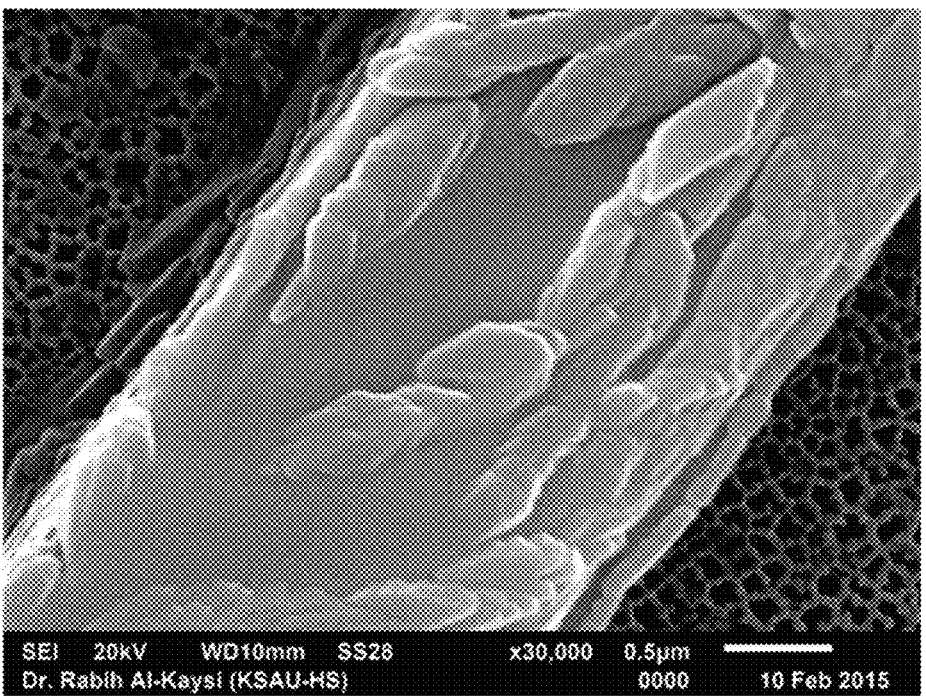
FIG. 8D shows an SEM image of the microblock of FIG. 8C, after irradiation without the presence of surfactant.
Figure 9A:
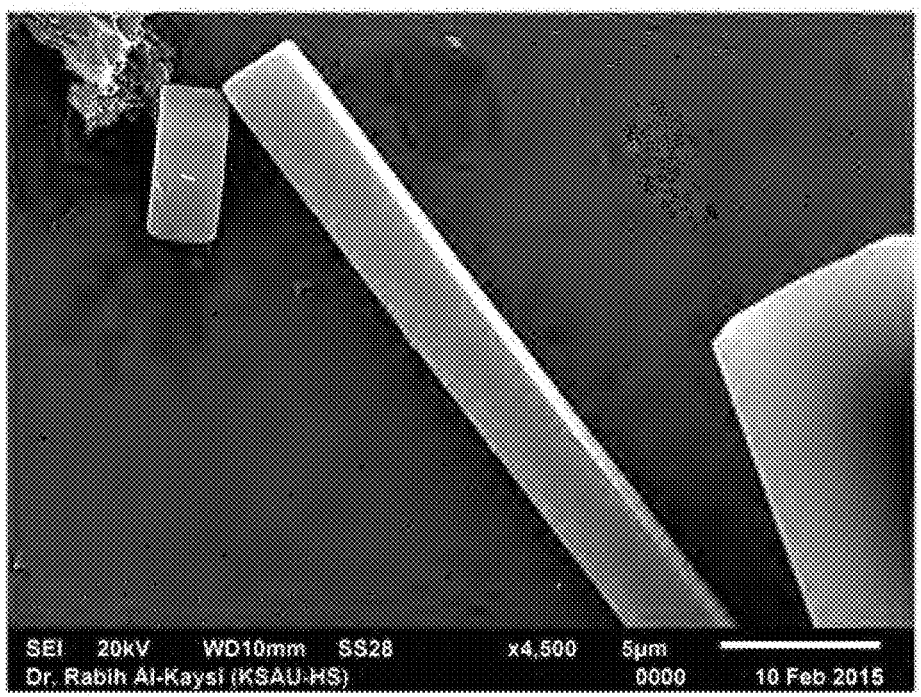
FIG. 9A shows an SEM image of cis-DMAAM µ-blocks after irradiation in the presence of surfactant and showing smooth surfaces.
Figure 9B:
FIG. 9B shows an SEM image of peeling cis-DMAAM µ-blocks after irradiation.
Figure 9C:
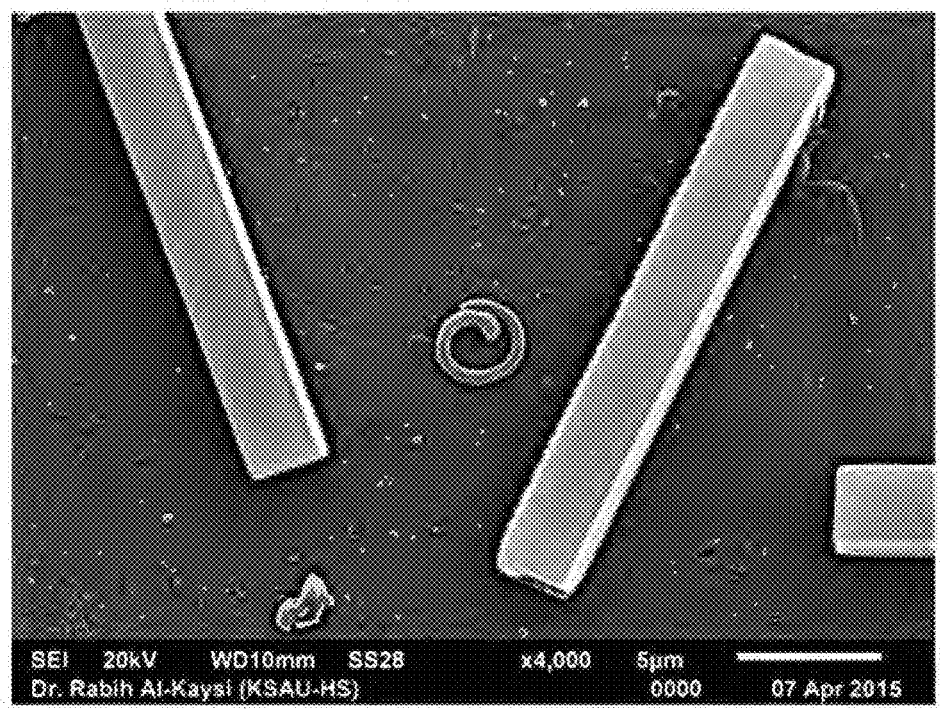
FIG. 9C shows another SEM image of peeling cis-DMAAM µ-blocks after irradiation.
Figure 9D:
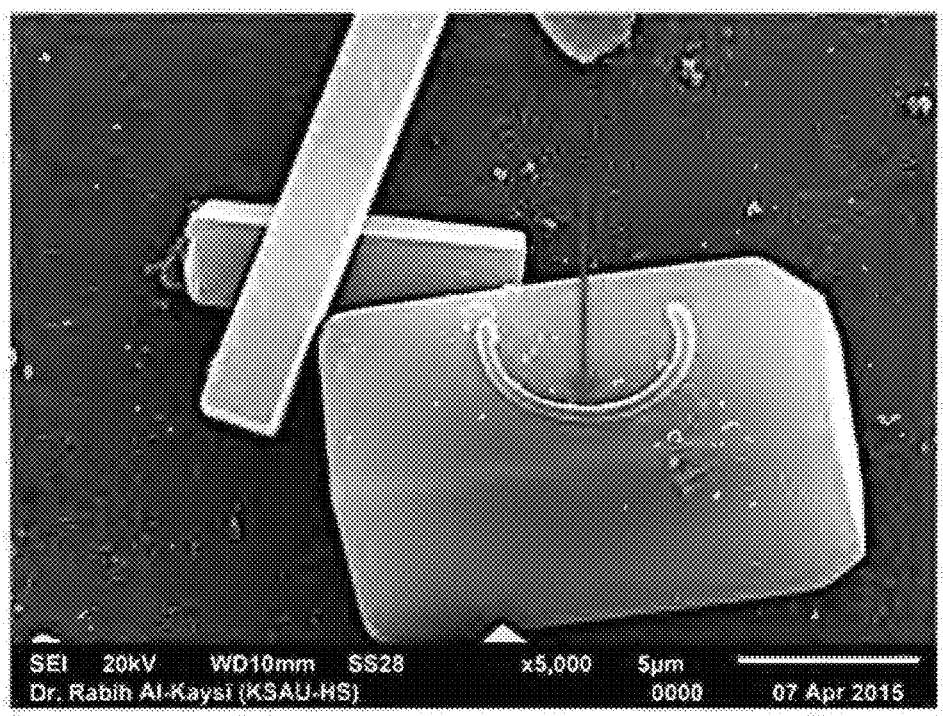
FIG. 9D shows another SEM image of peeling cis-DMAAM µ-blocks after irradiation.

FIGS. 7A-7D shows zoomed-out optical microscopy images of the peel sequence. Each frame represents a pulse of 405 nm light (100 mW/cm$^2$) with <1 sec duration. FIG. 7D represents the final sequence after 5 pulses. Scale bar is 25 μm FIGS. 8A-8D show images of a 13 μm-thick microbar undergoing irradiation without the presence of a surfactant. Here, the irradiation causes the surface to wrinkle, rather than delaminate. FIG. 8A-B, scale bar is 25 μm.

FIGS. 9A-9D show SEM images of the peeled surfaces and the peels (curled up structures).

Figure 10A:
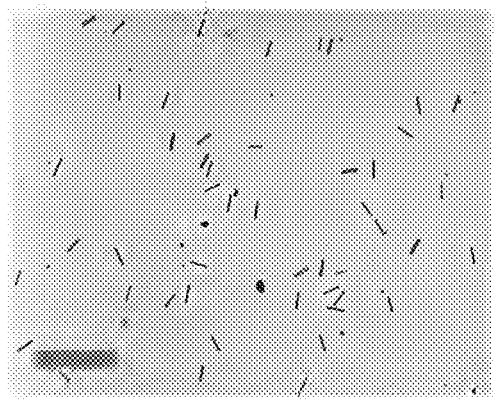
FIG. 10A shows an optical microscopy image of cis-DMAAM µ-blocks grown using a certain number of seeds from the µ-blocks of FIG. 2G.
Figure 10B:
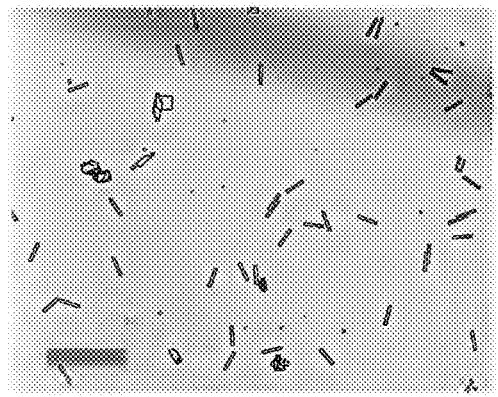
FIG. 10B shows an optical microscopy image of cis-DMAAM µ-blocks grown using twice the number of seeds used in FIG. 10A.
Figure 10C:
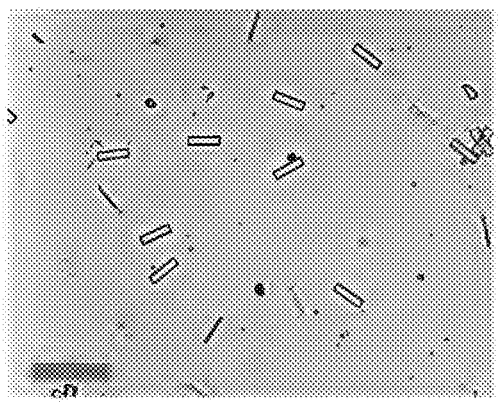
FIG. 10C shows an optical microscopy image of cis-DMAAM µ-blocks grown using three times the number of seeds used in FIG. 10A
Figure 10D:
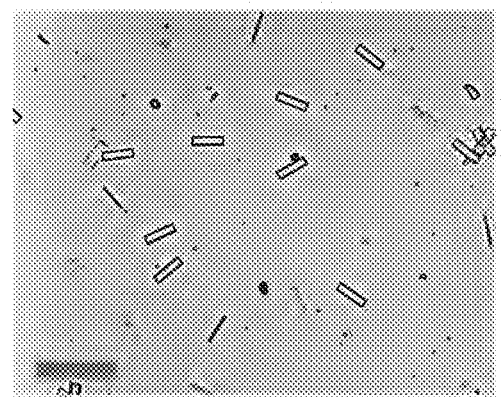
FIG. 10D shows an optical microscopy image of cis-DMAAM µ-blocks grown using 10 times the number of seeds used in FIG. 10A.
Figure 11A:
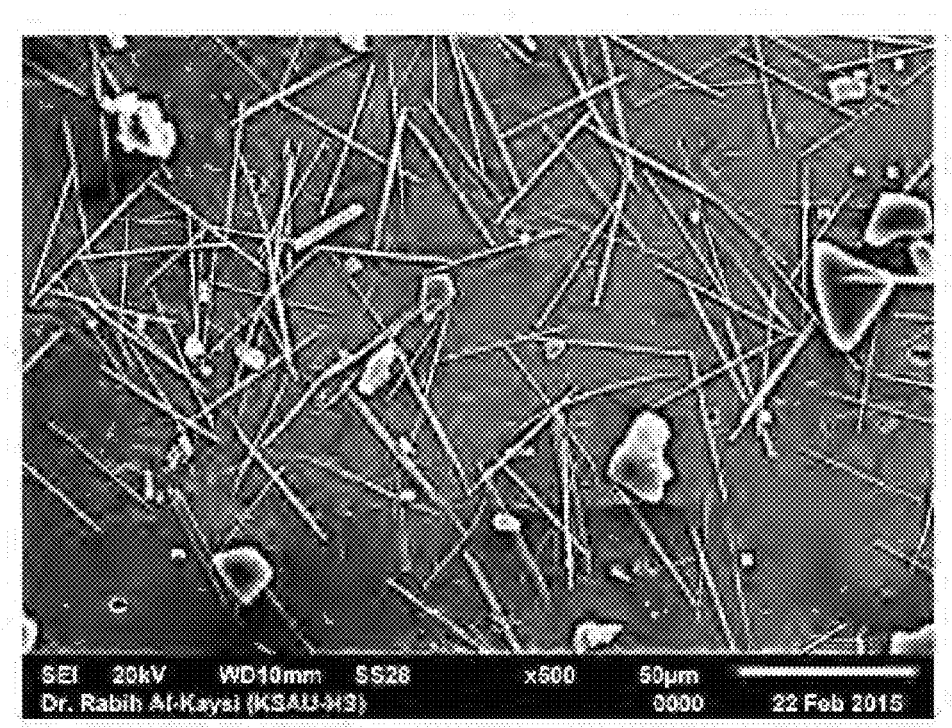
FIG. 11A shows an SEM image of cis-DMAAM microwires grown from 7.5 M phosphoric acid and 0.017 M SDS.
Figure 11B:
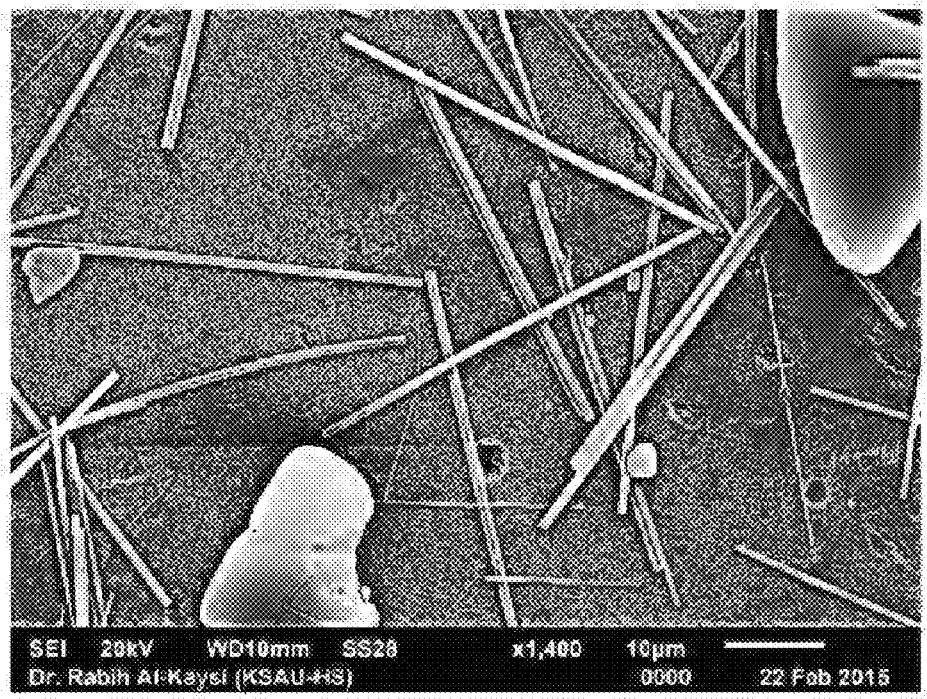
FIG. 11B shows another SEM image of cis-DMAAM microwires grown from the same conditions as FIG. 11A.
Figure 11C:
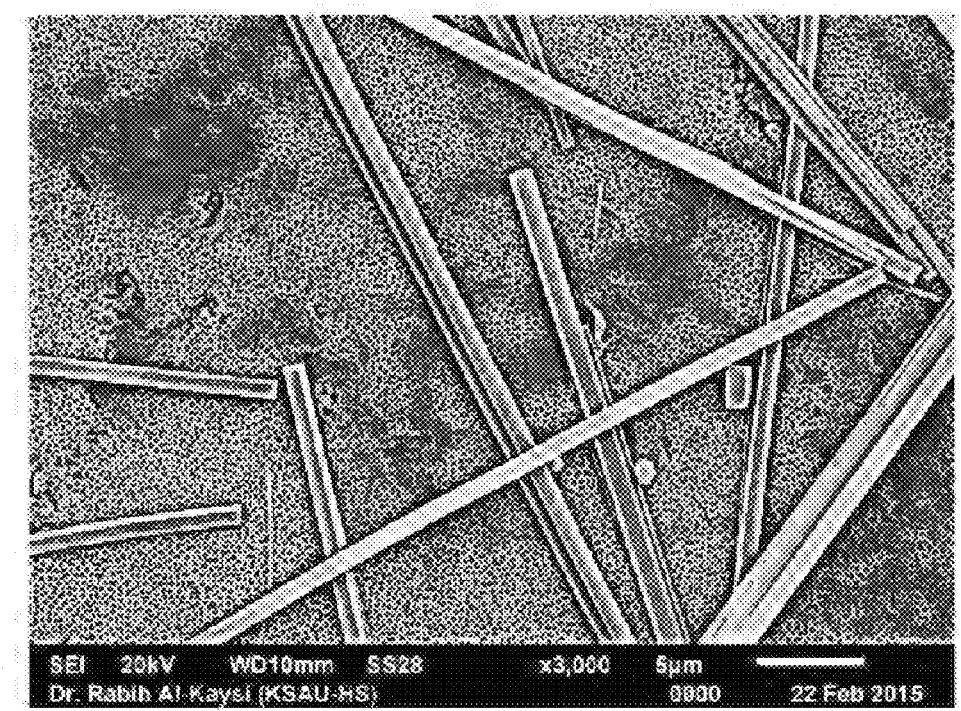
FIG. 11C shows an SEM image of cis-DMAAM microwires grown from the same conditions as FIG. 11A.
Figure 11D:
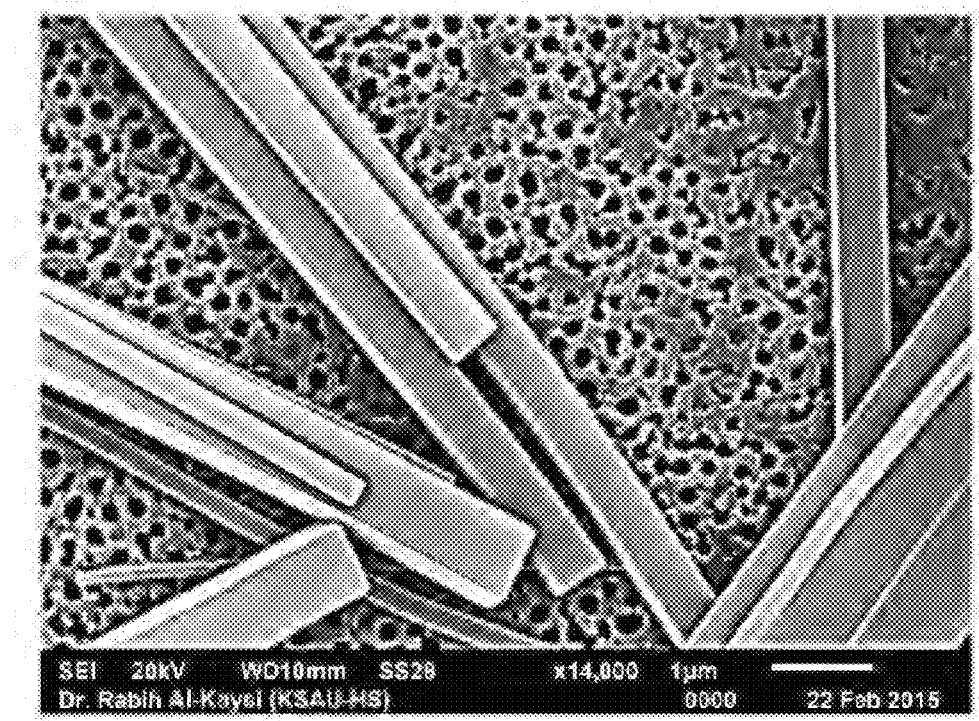
FIG. 11D shows an SEM image of cis-DMAAM microwires grown from the same conditions as FIG. 11A.

FIGS. 10A-10D show optical microscopy images of cis-DMAAM microblocks grown using different seeding times. FIG. 10A initial time, formation of small seeds. FIG. 10B-D increasing incubation time. All panels have the same magnification. Scale bar is 25 μm.

FIGS. 11A-11D show SEM images of cis-DMAAM microwires grown from 7.5 M phosphoric acid and 0.017 M SDS.

Figure 12:
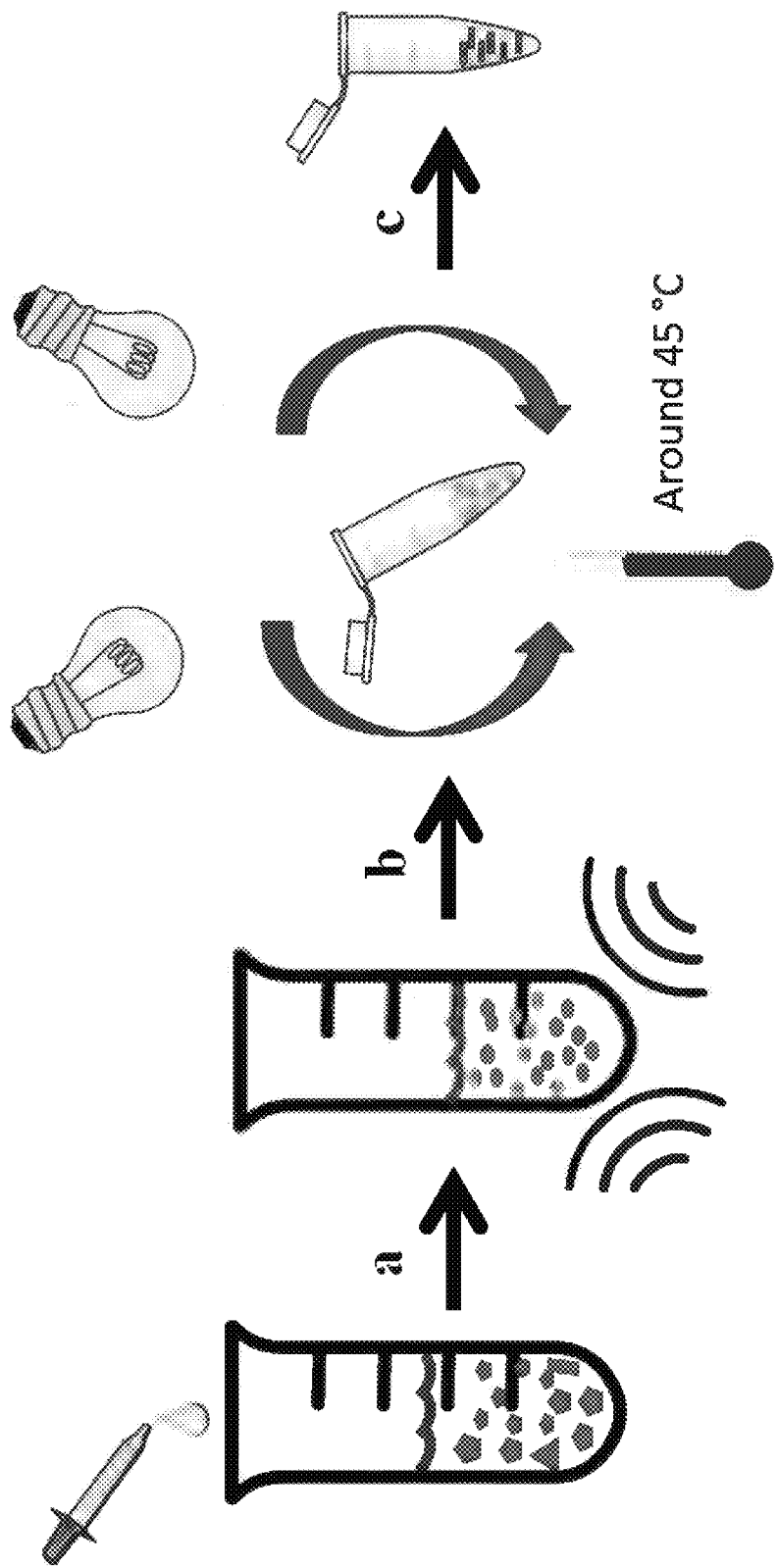
FIG. 12 illustrates another method for preparing cis-DMAAM µ-blocks.

FIG. 12 illustrates another method for preparing cis-DMAAM microblocks. In step "a," co-precipitation is initiated with the addition of 50 μL trans-DMAAM solution (0.35 M trans-DMAAM in N,N-DMF) to 10 mL of an aqueous 0.017 M SDS solution. Trans-DMAAM microplates are broken up using a probe-tip sonicator. In step "b," the solution is transferred to a 1.5 mL centrifuge tube (i.e. EPPENDORF tube) and rotated at 36 RPM while under incandescent lamp irradiation and a temperature of about 45° C. In step "c," the cis-DMAAM microblocks are formed.

Figure 13:
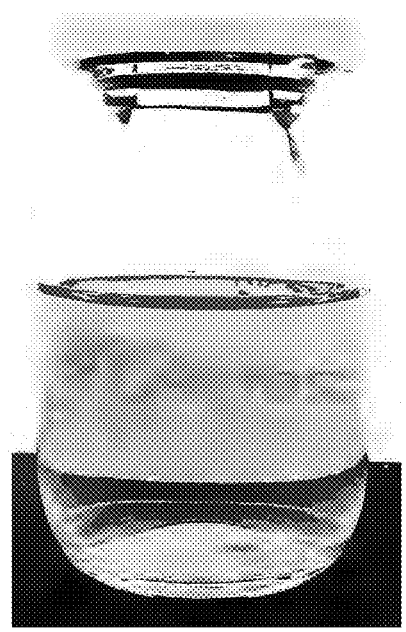
FIG. 13 shows a solution after 48 hours of incubation at 47° C., showing the formation of microwires.

FIG. 13 shows a bottle of cis-2-(3-(anthracen-9-yl)allylidene)malononitrile (cis-9DVAM) microwires forming as red, hair-like fibers suspended in mid solution.

Figure 14:
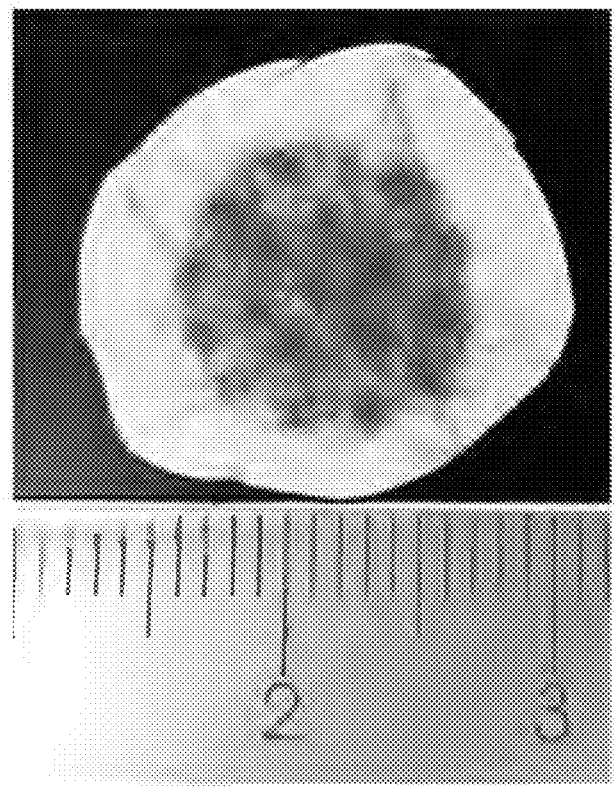
FIG. 14 shows an image of microwires after filtering onto filter paper.
Figure 15A:
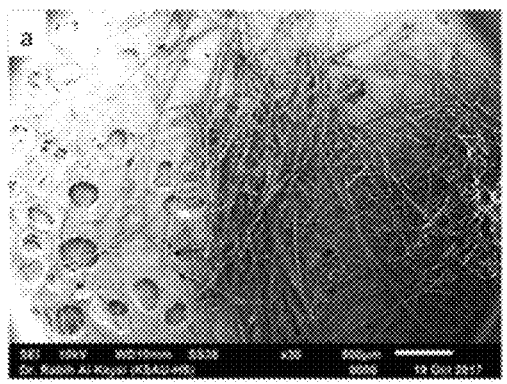
FIG. 15A is an SEM image of the microwires at a magnification of ×30.
Figure 15B:
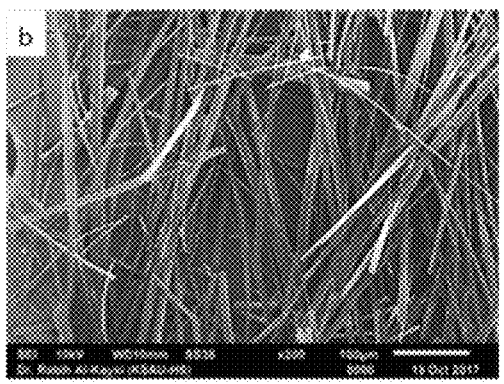
FIG. 15B is an SEM image of the microwires at a magnification of ×200.
Figure 15C:
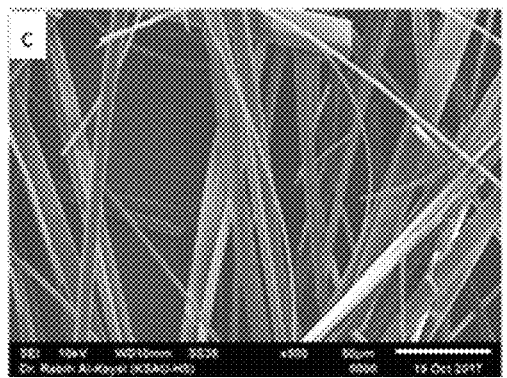
FIG. 15C is an SEM image of the microwires at a magnification of ×500.
Figure 15D:
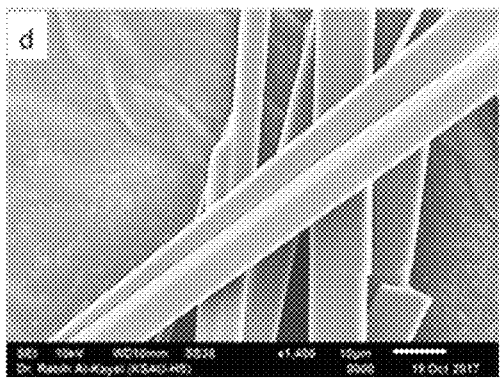
FIG. 15D is an SEM image of the microwires at a magnification of ×1400.

FIG. 14 shows the filtered microwires from the solution in FIG. 13.

FIGS. 15A-D shows SEM images of the microwires deposited over conductive carbon tape and coated with a thin layer of Pt. FIGS. 15A, 15B, 15C, 15D are at magnifications of ×30, ×200, ×500, and ×1400, respectively.

Figure 16:
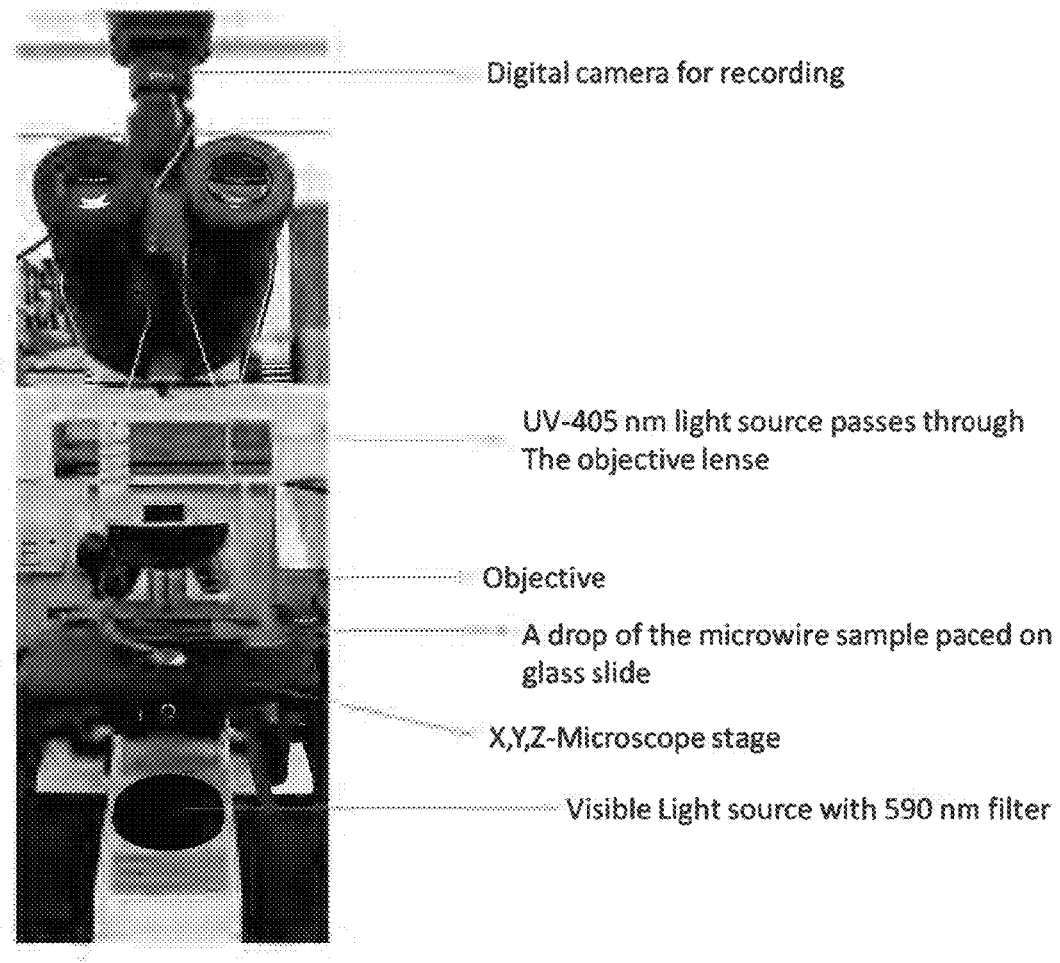
FIG. 16 is an example microscope setup for the observation of light-induced microwire motion under continuous irradiation.

FIG. 16 shows an example microscope setup for the observation of light-activated motion in the microwires.

The examples below are intended to further illustrate protocols for forming and exfoliating the microcrystal of formula I, and uses thereof, and are not intended to limit the scope of the claims.

Example 1

Sample Preparation

Electrophoresis grade SDS (>98.5%) was purchased from Bio Rad and used without further purification. 1-Dodecanol (98%) was purchased from Sigma Aldrich and used without further purification. N,N-DMF was distilled before use. MILLI-Q water was used for all the experiments and dilutions. Cis-DMAAM (96% cis isomer) was prepared following a previously reported procedure. See Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi:10.1002/anie.201302323—incorporated herein by reference in its entirety. To prepare uniform shaped microcrystals, an aqueous solution comprising 0.02 M Sodium Dodecyl Sulfate (SDS) was prepared with varying amounts of 1-dodecanol. A cis-DMAAM solution in distilled N,N-dimethylformamide (0.13 M, 25 μL) was injected into 5 mL of the SDS/1-dodecanol solution warmed to 40° C. while stirring at 1500 rpm inside a 30 mL glass vial. Without 1-dodecanol in solution, elongated octahedral microcrystals (tetragonal dipyramidal) form and separate out after one hour of stirring. For high 1-dodecanol concentrations (>0.0022 M), uniform μ-blocks (tetragonal prisms) form and precipitate out after one hour of stirring. On average, the L-block dimensions are on the order of 10 μm long and 1 μm wide with 8% standard deviation.

In order to obtain larger crystals of either habit (rectangular or octahedral), 25 μL of the cis-DMAAM solution was injected in the SDS or SDS/1-dodecanol solution (5 mL, 40° C.) without vigorous stirring. This yields a quasi-stable solution of cis-DMAAM that remains clear for several hours when undisturbed. For larger μ-blocks, a 25 μL suspension of the previously prepared μ-blocks was added to this quasi-stable solution in a 30 mL vial to seed crystal growth. The mixture was slowly tumble rotated at 40° C. for 24 hours. μ-blocks grown in this way are roughly 30× larger in volume. Larger μ-blocks were formed when fewer seeds were introduced. When the quasi-stable solution was left unseeded, undisturbed, and at 40° C. for several days, jumbo-sized blocks were formed with a hole on the end faces, as shown in FIGS. 3B and 3C. The crystal size and shape outcomes from a variety of different growth conditions are described in Table 1.

Example 2

Characterization

SEM measurements were performed using a JEOL JSM-6510LV scanning electron microscope. Samples were coated with a thin layer of Pt prior to scanning. Optical microscopy studies were performed using an upright OPTIKA brand fluorescence microscope equipped with a 2 MP digital camera. A drop of the cis-DMAAM μ-blocks was deposited over a microscope glass slide then covered with a coverslip. To initiate the photomechanical response, the sample was pulsed with light from a 100 W medium pressure Hg lamp passing through a bandpass (475 nm, 405 nm or 365 nm) filter from Edmund Optics with a full width-half max of 10 nm. A 1 s pulse was enough to cause the μ-blocks to spontaneously peel after 15 to 20 s, regardless of their size.

HPLC analysis of the photoproducts was performed on peels obtained by pulsing a 5 μL suspension of the μ-blocks in SDS/1-dodecanol with 405 nm light until the entire sample consisted of peels. The suspension was dissolved in acetonitrile and analyzed using HPLC (Shimadzu Japan) with a C18 reverse phase general purpose column and a mobile phase consisting of 80% o acetonitrile 20% water at pH=2.

Example 3

Results and Discussion

When cis-DMAAM crystals are grown by slow ethanol/water solvent evaporation, large millimeter size plate-like crystals are obtained that are suitable for single crystal structure determination. When these crystals are exposed to UV light, they develop cracks and undergo fragmentation at the edges as typically seen in large-size photoreactive crystals. This type of photoinduced crystal deterioration is commonly observed in large photoreactive crystals that do not have the ability to relieve strain generated by the photoreaction on the surface. In order to obtain a more useful photomechanical response, a seeded growth procedure in an aqueous solution was used (FIG. 1). The aqueous solution comprises a mixture of sodium dodecyl sulfate (SDS) and 1-dodecanol.

It was found that varying the concentration of the 1-dodecanol had a dramatic effect on the microcrystal shape. FIGS. 2A-2J show a series of SEM images of cis-DMAAM microcrystals grown at increasing 1-dodecanol concentrations ([1-$C_{12}$OH]) with [SDS]=0.02 M. For [1-$C_{12}$OH]=0.0, elongated octahedral crystals were obtained. As [1-$C_{12}$OH] was increased, new crystal facets appeared that formed a rectangular body capped by pyramidal ends. These tetragonal prisms gradually evolved into well-defined block-like prism crystals with increasing aspect ratio for the highest values of [1-$C_{12}$OH]. Keeping the temperature around 40° C. was required in order to keep the water insoluble 1-dodecanol dissolved in the SDS solution and to prevent it from co-crystallizing with SDS.

If the solution was not agitated, large blocks of cis-DMAAM crystals out with holes on either end over a period of several days, as shown in FIGS. 3B and 3C.

The ultimate width and length of the blocks could be tuned by varying the values of [SDS], [1-$C_{12}$OH], and the agitation conditions, and the complete transformation from octahedral to tetragonal prism shapes was very robust as long as [1-$C_{12}$OH]>0.001 M. Substituting 1-dodecanol with longer chain alcohols like 1-octadecanol, or 1H,1H,2H,2H-perfluoro-1-dodecanol did not yield pi-blocks, but instead randomly-sized pyramid terminated prisms.

The ability of surfactants to modify the shapes of organic crystals grown by reprecipitation in an aqueous solution has been observed by previous workers. While a detailed mechanistic understanding of this phenomenon is still lacking, there is a general consensus that stabilization of different crystal faces by different surfactants plays a key role. In these crystals, PXRD was used to identify the crystal plane associated with the flat sides of the tetragonal prisms. By careful removal of surfactant followed by drying, it is possible to make samples in which the blocks are lying horizontal along their long axis on the substrate and then perform a PXRD measurement to determine their crystal orientation. This measurement, shown in FIG. 5A, allows the determination of which Miller planes lie parallel to the substrate and thus the crystal orientation. It is hypothesizes that increasing 1-dodecanol concentration binds to the faces of the elongated octahedron limiting their growth and thus promoting the growth of other facets.

For stable organic molecules, the growth of microcrystals with varying shapes may be useful for assembly or shifting fluorescence. But for photoreactive molecules like cis-DMAAM, changing the crystal shape can lead to qualitatively new modes of photomechanical action. For example, when the octahedral crystals are exposed to 405 nm light, there is some evidence of surface roughening and partial delamination, but in many cases there is no visible change at all. Even though the surface layers are probably undergoing cis to trans photoisomerization, the large thickness of these crystals prevents the curling seen in the nanowires. However, the irradiation of a different crystal face on block-like crystals leads to a novel response: the photoinduced peeling of surface layers. FIGS. 6A-6D illustrate a sequence of events: the crystal block is first exposed to a flash of 405 nm light from a 100 W medium pressure Hg lamp (100 mW/cm$^2$) for a duration of 1 s. After this exposure, a longitudinal section begins to delaminate and curl against the parent crystal, finally detaching from the main block within 10-20 s of the irradiation. This process can be repeated multiple times until the original block is completely delaminated. For 1 s pulse durations, a block that is originally 3 μm thick will yield ~6-7 peels, and assuming the peels have similar thicknesses, the thickness of each delaminated layer is ~400 nm. To study and asses the effect of pulse duration on the number of peels produced, a semi quantitative experiment was performed on μ-blocks with a 2.4 μm cross-section. For 1 s pulses, on average 6 peels were observed; when the pulse duration was doubled to 2 s, 4 peels in total were liberated; and when the pulse duration was extended to 5 s, roughly 2 peels were observed. Thus, the longer the pulse, the thicker the peel formed and the longer it takes for the peel to detach from the mother crystal.

Micro-blocks with a cross-section <700 nm tend to spontaneously coil instead of peel, while continuous irradiation will cause them to expand by up to 60% their original length. In addition, continuous irradiation of thicker t-blocks causes them to expand and flatten. The presence of SDS in solution was necessary for the peels to fully detach from the parent crystal. When the SDS was removed after centrifugation and the microblocks were resuspended in pure water, surface distortions and partial delamination was observed, but not the clean detachment seen in the SDS solution. An example of these surface distortions is shown in FIGS. 8A-8D.

The observation of sequential photoinduced peeling from a molecular crystal represents a qualitatively new mode of photomechanical response. It can be thought of as a controlled fracture event that is reproducible thanks to the well-defined shape of the reactant crystals. Flat trans-DMAAM hexagonal microplates, which are produced using similar precipitation protocol, do not show the same delamination mechanism after pulsing them with light. The detailed mechanism of the peeling is not known. The photoreacted cis-DMAAM microcrystals were analyzed using HPLC and were found to consist of 10-20% trans-DMAAM. This is consistent with previous measurements on photoreacted nanowires and is evidence that the photoisomerization does not proceed to 100% completion but instead reaches a photostationary state that limits the total conversion to the trans isomer. The peeled photoproduct itself is not crystalline, as judged by its lack of any discernible X-ray or electron diffraction peaks.

Photomechanical peeling of cis-DMAAM is the outcome of a unique collaboration between an amorphous photoisomerized layer and presence of surfactant. When a microblock is exposed to a short pulse of 405 nm light, photoisomerization of a ~500 nm thick layer turns it into an amorphous region that has lower density than the rest of the crystal. This difference in packing density prevents the molecules in the amorphous peel from diffusing in and causes it to phase separate. Under normal circumstances this layer adheres to the surface due to hydrophobic or van der Waals attraction. This phase separation is further enhanced by the presence of SDS which acts as a lubricant sliding between the crystal and the newly formed peel. A possible mechanism for the peeling involves photoisomerization followed by shrinkage of an outer layer of amorphous photoproduct. Irradiation of the blocks preferentially reacts one side to form a mixture of cis and trans isomers. After the light is turned off, over several seconds the reacted slab rearranges and contracts, causing it to delaminate from the parent block. It was noted that the peels generally curl inward, with the middle detaching first and the ends detaching last. This type of photoinduced curling is also seen in nanowires and microribbons composed of the same molecule. Isotropic shrinkage often results in curling due to local stresses that build up in the material. The fact that such a clean break occurs with the parent block may be the result of phase separation between the reacted and unreacted regions, followed by shrinkage of the reacted region and finally delamination. The delay between the initial light exposure and when peeling is observed may reflect the time required to form this new product phase by molecular migration within the block. This sequence of events is outlined in FIGS. 6A-6D.

The results of these experiments illustrate that surfactants can control the growth of a photoreactive molecular crystal. The high 1-dodecanol/SDS concentrations allow the growth and enhancement of certain facets of well-defined µ-blocks of cis-DMAAM. When exposed to a burst of 405 nm light, these blocks exhibit a new type of photomechanical response: well-defined peeling in which a 500 nm thick slab of the crystal delaminates from the parent block. This peeling is caused by a rapid expansion of the mixed cis-trans amorphous phase, and the peels continue to curl even after detaching from the block. This phenomenon serves as another illustration of how controlling crystal morphology (size and shape) can lead to novel modes of mechanical behavior. Although its detailed mechanism has yet to be elucidated, this new type of photomechanical response may be useful for applications like self-cleaning or self-renewing surfaces.

Example 4

Full Description for the Preparation of Cis-DMAAM Compound

Cis-DMAAM compound was prepared following a procedure previously. See Kim, T.; Al-Muhanna, M. K.; Al-Suwaidan, S. D.; Al-Kaysi, R. O.; Bardeen, C. J. Photoinduced Curling of Organic Molecular Crystal Nanowires. *Angew. Chemie Int. Ed.* 2013, 52, 6889-6893, doi: 10.1002/anie.201302323—incorporated herein by reference in its entirety. Briefly, trans-DMAAM (50 mg) was dissolved in 50 mL of ethanol and stirred under intense incandescent lamp light for several hours, followed by addition of 50 mL of D.I. water and stirring under the same conditions for another 24 hours. Cis-DMAAM with >96% pure cis isomer precipitates out in a quantitative yield. All aqueous solutions were prepared using D.I. water and filtered through 0.45 m pore size nitrocellulose filter prior to use. N,N-DMF was distilled prior use.

A—Preparation of Cis-DMAAM µ-Octahedral Crystals.

Cis-DMAAM solution in distilled N,N-DMF (0.13 M, 25 µL) was injected into an aqueous SDS solution (5 mL, 0.02 M, 40° C.) while stirring at 1500 rpm inside an 8 dram vial. µ-Octahedral cis-DMAAM crystals separate out after one hour of stirring. In order to obtain larger µ-Octahedral crystals, 25 µL of the cis-DMAAM solution is injected in the aqueous SDS solution (5 mL, 0.02 M, 40° C.) but this time without stirring. A quasi stable solution is formed as long as it is not stirred or agitated. A 25 µL suspension of the previously prepared µ-Octahedrals was added to the quasi stable solution inside an 8 dram vial and tumble rotated at 40° C. for 24 hours. The added suspension of µ-octahedral crystals acts as seeds onto which more cis-DMAAM is deposited.

B—Preparation of Cis-DMAAM µ-Logs.

Cis-DMAAM solution in distilled N,N-DMF (0.13 M, 25 µL) was injected into a stirring solution of aqueous SDS/1-dodecanol (5 mL, 0.02 M SDS/0.0022 M 1-dodecanol, 40° C., 1500 rpm). Initially the mixture forms a quasi-stable solution that slowly crashed out into uniform µ-logs after >60 minutes. Several SDS/1-dodecanol formulations along with phosphoric acid was used to obtain different sized µ-log crystals. A table describing conditions and resulting µ-log dimensions is provided in Table 1. On average, the µ-log dimensions are on the order of 10 µm long and 1 µm wide with 8% standard deviation. In order to grow larger µ-logs, a modified procedure B was followed. After injecting the cis-DMAAM solution, stirring was stopped immediately and the temperature kept at 40° C. This will give a quasi-stable solution of the cis-DMAAM in aqueous SDS/1-dodecanol that will remain stable for several hours as long as it is not disturbed. 25 µL of the µ-log suspension from part B was gently injected in the metastable solution and the vial given a gentle swirl. The temperature was decreased to 40° C. Larger µ-logs grow from the seeded µ-logs over a period of several hours. The average size of the formed µ-logs is roughly 30× larger in volume.

C—Formation of Peels.

A drop of the cis-DMAAM µ-logs was deposited over a microscope glass slide then covered with a coverslip. An upright fluorescence microscope was used (OPTICA) in order to pulse the sample with visible light (405 nm) from a 100 W medium pressure mercury lamp. A short 1 s pulse was used, and the µ-logs spontaneously peeled within 15 to 20 s.

31

D—Analysis of the Peels.

A 5 µL suspension of the pt-logs in SDS/1-dodecanol was pulsed with 405 nm light several times until the entire sample was peeled off. The suspension was dissolved in acetonitrile and analyzed using HPLC (Shimadzu) with a C18 general purpose column having a mobile phase consisting of 80% acetonitrile 20% water with a pH=2.

TABLE 1

Conditions that yield different size µ-logs: Unless stated, [cis-DMAAM] is 0.13M, volume of aqueous mixture = 5 mL, and volume of cis-DMAAM solution injected = 25 µL.

| [SDS], M | [1-dodecanol], M | [$H_3PO_4$], M | µ-log: Length × Width (µm) and (Volume, µm$^3$) | Temperature, °C |
|---|---|---|---|---|
| 0.02 | 0 | 0 | µ-octahedrons | 40 |
| 0.02 | 0.001 | 0 | Truncated µ-tetragons | 60 → 40 |
| 0.02 | 0.0022 | 0 | µ-log: 10.5 × 1.5 (V = 24) "G1" | 60 → 40 Slow stirring 400 rpm |
| 0.02 | 0.0022 | 0 | µ-log: 12.1 × 2.1 (V = 53) G2: 1 mg of seeds from previous run were used | 60 → 40 Tumble rotate |
| 0.02 | 0.0044 | 0 | µ-log: 13.2 × 1.1 (V = 16) | 60 → 40 |
| 0.02 | 0.0066 | 0 | µ-log: 15.3 × 1.3 (V = 26) | 60 → 40 |
| 0.02 | 0.0022 | 0 | µ-log: 6 × 1.1 (V = 7) | 40 Stirring at 1500 rpm |
| 0.02 | 0.0022 | 0 | µ-log: 15 × 4 (V = 240) | 40 Unstirred |
| 0.02 | 0.0033 | 0 | µ-log: 8.5 × 1.1 (V = 10) | 40 |
| 0.02 | 0.01 | 0 | µ-log: 11.4 × 1.2 (V = 16) | 40 |
| 0.01 | 0.0022 | 0 | µ-log: 5.1 × 1.1 (V = 6) | 40 |
| 0.01 | 0.0033 | 0 | µ-log: 7 × 1.3 (V = 12) | 40 |
| 0.02 | 0.02 | 7.5 | Very thin <700 nm | 40 |
| 0.01 | 0.0033 | 3.5 | µ-log: 8.2 × 1.0 (V = 8) | 40 |
| 0.01 | 0.0033 | 3.5 | µ-log: 18 × 4 (V = 288) | 40 (tumble rotate) |

Example 5

Alternative Method for the Preparation of Cis-DMAAM µ-Blocks

The following is a detailed, step-by-step procedure of how to prepare cis-DMAAM µ-Blocks using a white light LED panel from Edmund optics.

Materials

Trans-DMAAM, Sodium Dodecyl Sulfate (SDS), DI water, N,N-DMF (reagent grade).

Equipment and Supplies

A probe sonicator, convection oven set at 45° C., white light LED panel, EPPENDORF PCR tubes (0.5 mL capacity) clear walls, not frosted.

Procedure

Between 4 to 5 mg of trans-DMAAM in is dissolved in 50 µL of N,N-DMF. A 0.5% SDS solution in water is made by dissolving 0.05 g SDS in 10 mL of DI water. The SDS solution is stirred at 40° C. in an 8 dram (around 30 mL) vial, while the trans-DMAAM solution is added. The solution is immediately sonicated using a probe tip sonicator for 30 to 60 s, or until the suspension color turns from orange to bright yellow.

Next, 0.2 mL of the sonicated suspension is deposited in each EPPENDORF tube and shaken gently (5 tube samples is good enough). The EPPENDORF tubes are placed flat on a white LED panel inside an oven set at 45° C., and the tubes are allowed to equilibrate to the temperature for 10 minutes before turning on the panel. The oven may be set to a lower temperature, such as 35° C., as long as the temperature is high enough to prevent precipitation of the SDS. After temperature equilibration the LED panel is turned on for 30 minutes, after which the tubes are removed and observed for block formation by opening the lid for 3 minutes. This process also lets in a tiny amount of air, which helps to dissolve the SDS in the tube and nucleate crystals of cis-DMAAM. The tubes may be shaken before being placed on the panel again for another 30 min. In addition, the tubes are shaken every 15 min, and without opening the tubes, in order to prevent the trans-DMAAM particles from settling at the bottom. The tubes may be opened again to sample for blocks, and this process may be repeated every 30 min. After a total of 2 hours micro-block formation should be visible. The reaction may be stopped when the microparticle suspension of trans-DMAAM is no longer visible under the microscope. The microblock thickness may be modified based on the amount of time that the tube is opened and the manner of shaking or agitating the solution.

Example 6

Light-Induced Autonomous and Pseudo-Perpetual Motion of Molecular Crystal Microwires Material that can actuate in response to an external stimulus and in turn move or manipulate tiny objects has application in areas such as manufacturing of small parts or as autonomous microrobotic surgeons. See Naumov, P.; Chizhik, S.; Panda, M. K.; Nath, N. K.; Boldyreva, E. Mechanically Responsive Molecular Crystals. *Chem. Rev.* 2015, 115, 12440-12490, doi:10.1021/acs.chemrev.5b00398, and Kim, T.; Zhu, L.; Al-Kaysi, R. O.; Bardeen, C. J. Organic photomechanical materials. *Chemphyschem* 2014, 15, 400-14, doi:10.1002/cphc.201300906, each incorporated herein by reference in their entirety. In general, most actuators that are found in machines and electronic devices have to be in physical contact with a power supply, via electrically conducting wires, in order to function. Here, actuators are designed to instead function without being in physical contact with a bulkier control module or being dependent on chemical fuel supplied by the surrounding environment. In this case, photons are the ideal tool for controlling and providing power for nanoscale and microscale non-contact actuators, since they can access a wider variety of media and transport both energy and information by varying the wavelength and intensity of the incident photon. Photon or light-powered actuators are capable of directly converting light into mechanical work without first converting the light energy into electrons, via a photocell, in order to power tiny electrical actuators. This conversion is possible with molecules that can transform light energy into motion by absorbing photons or undergoing photochemical reactions that lead to bonds breaking, forming, or otherwise reconfiguring a molecule's geometry. This leads to the conversion of light absorption into mechanical work.

In 2016, Sir J. Fraser Stoddart, Bernard L. Feringa, and Jean-Pierre Sauvage were awarded the Nobel Prize in Chemistry for their work on the synthesis and applications of molecular machines. As the name implies, these molecular machines function on the molecular level, hence detecting any kind of motion or work from them requires highly sophisticated instruments such as Nuclear Magnetic Resonance (NMR), spectrofluorometry, spectrophotometry, magnetic susceptibility detection, etc. These molecular machines require direct contact with an external stimulus in the form of protons (pH-triggered) or electrons (redox reaction triggered), with the disadvantage of their response speed being limited by diffusion kinetics. In our work, we intend to couple light responsive molecular machines together and make them trigger simultaneously upon light exposure. This enables their photomechanical response to be detected using nothing more than an optical microscope or sometimes the naked eye. Here, molecular crystal systems exhibit photochemical changes that generate mechanical motion on length-scales that are orders of magnitude greater than the molecular dimensions. See Zeng, H.; Wasylczyk, P.; Parmeggiani, C.; Martella, D.; Burresi, M.; Wiersma, D. S. Light-Fueled Microscopic Walkers. *Adv. Mater.* 2015, 27, 3883-3887, doi:10.1002/adma.201501446; Fujii, K.; Uekusa, H.; Fukano, M.; Koshima, H. Metastable polymorphic form of isopropylbenzophenone derivative directly obtained by the solid-state photoreaction investigated by ab initiopowder X-ray diffraction analysis. *CrystEngComm* 2011, 13, 3197-3201, doi:10.1039/C0CE00500B; Zhu, L.; Al-Kaysi, R. O.; Bardeen, C. J. Photoinduced Ratchet-Like Rotational Motion of Branched Molecular Crystals. *Angew. Chemie Int. Ed.* 2016, 55, 7073-7076, doi:10.1002/anie.201511444; Bushuyev, O. S.; Singleton, T. a; Barrett, C. J. Fast, reversible, and general photomechanical motion in single crystals of various azo compounds using visible light. *Adv. Mater.* 2013, 25, 1796-800, doi:10.1002/adma.201204831; and Yu, Y.; Nakano, M.; Ikeda, T. Photomechanics: Directed bending of a polymer film by light. *Nature* 2003, 425, 145-145, doi: 10.1038/425145a—each incorporated herein by reference in their entirety.

In these photo-responsive materials, the ordered arrangement of the photochemically reactive units or photochromes can be utilized to amplify the geometry changes on the molecular level, thus leading to observable and measurable macroscopic deformation. In other words, since all the photochemical reactions inside the ordered crystal are happening at the same time and in the same direction, the tiny amount of work energy generated from one molecule will be collectively amplified and summed up to give a measurable impact. Such photomechanical crystals can be used to directly convert light energy into mechanical motion and can potentially become active elements in light-activated actuator devices. By changing the shape of the photomechanical crystal, its photomechanical response and direction of action may be changed. For example, photomechanical crystal that is thin and wide (ribbon-like) tend to twist when exposed to light, while needle-like crystals of made from the same material will simply bend when excited with the same amount and wavelength of light. See Kim, T.; Zhu, L.; Mueller, L. J.; Bardeen, C. J. Mechanism of Photoinduced Bending and Twisting in Crystalline Microneedles and Microribbons Composed of 9-Methylanthracene. *J. Am. Chem. Soc.* 2014, 136, 6617-6625, doi:10.1021/ja412216z., and Zhu, L.; Al-Kaysi, R. O.; Bardeen, C. J. Reversible photoinduced twisting of molecular crystal microribbons. *J. Am. Chem. Soc.* 2011, 133, 12569-12575, doi:10.1021/ja201925p—each incorporated herein by reference in their entirety.

Here, a photomechanical engine is formed by a high aspect ratio microwire crystal of a small molecule with an anthracene. Microwires suspended in an aqueous solution containing a surfactant may be made to wiggle, bend or rotate indefinitely when exposed to a continuous broad wavelength light source. The frequency of actuation may be enhanced by simultaneously illuminating the microwire from top and bottom with UV and visible light.

Materials (E)-3-(Anthracen-9-yl)acrylaldehyde and piperidine were purchased from TCI-America. Malonitrile was purchased from UFC Biotechnology Riyadh in Saudi Arabia. All reagents were used without further purification. All organic solvents were distilled over an appropriate drying agent and stored over activated molecular sieves (4 Å) prior to use. Due to the photosensitive nature of the products, the synthesis was performed under dim laboratory light conditions.

Instrumentation

Spectroscopic characterization of the organic molecules was done using H and C-NMR. Scanning electron microscopy was performed on a JEWEL. Optical microscopy and recording of the photo-induced motion of the molecular crystals was recorded on an OPTICA brand fluorescence microscope. Images and moves were recorded using a 2 megapixel camera at a 1600×1200 resolution.

Synthesis of Small Molecules:

For the synthesis consult the following chemical reaction scheme:

Reaction Schemes: (a) Synthesis of trans-9DVAM;
(b) trans-9DVAM ⟶ cis-9DVAM photoisomerization.

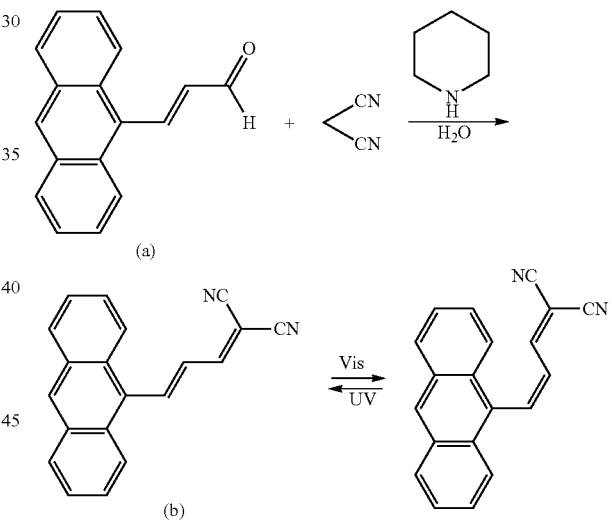

Trans-3-(anthracen-9-yl)acrylaldehyde (1.0 g, 4.3 mmol) was suspended in DI water (40 mL) along with malonitrile (1.0 g, 15 mmol, 3 equivalent) and a catalytic amount of piperidine (0.1 mL) inside a 100 mL round bottom flask. Ethanol (2 mL) was added to aid in the dispersion of the water-insoluble reactants. The reaction was ultrasonicated in a water-bath set at 70° C. for a period of 2 to 3 hours under an atmosphere of argon gas. The reaction mixture turned from brown-yellow to brick-red, indicating formation of product. The reaction progress was monitored by HPLC until all the reactant was consumed. The insoluble red-colored crude product was suction-filtered and washed with fresh water to remove the excess unreacted malonitrile. At this stage the crude product was more than 97% pure. Recrystallization from 1-propanol (45 mL) gives pure red-colored short microribbon crystals (1.12 g, yield=93%) with a M.P.=202-205° C., uncorrected. $^1$H-NMR in $CDCl_3$ d (ppm): 7.30-7.48 (dd, 1H), 7.50-7.69 (m, 4H), 7.87-7.91 (d, 1H), 8.03-8.05 (d, 2H), 8.16-8.19 (d, 2H), 8.32-8.36 (d, 1H), 8.52 (s, 1H).

Synthesis of cis-2-(3-(anthracen-9-yl)allylidene)malononitrile or cis-9DVAM

Trans-9DVAM (100 mg) was suspended in trifluoroacetic acid (25 mL) inside a 40 mL vial and purged using argon gas for 3 minutes. The vial was tightly sealed and vigorously stirred while being photolyzed by light from a 60 W medium pressure Hg lamp passing through a 590 nm long pass filter (Edmund Optics). Progress of the photolysis was monitored by HPLC until the reaction tapered off after 95% conversion to cis-9DVAM after 5 hours. The solvent was recovered under reduced pressure, and the oily residue was ultrasonicated with a mixture of 5 mL methanol and 40 mL of DI water. The cis-isomer was suction-filtered and air dried to yield 98 mg of cis-9DVAM (95% pure cis isomer) and a M.P. =157-159° C., uncorrected. $^1$H-NMR in CDCl$_3$ d (ppm): 7.07-7.15 (d, 1H), 7.35-7.39 (t, H), 7.50-7.55 (m, 5H), 7.85-7.89 (m, 2H), 8.04-8.09 (m, 2H), 8.55 (s, 1H).

Fabrication of the Cis-9DVAM Microwires:

Preparation of the aqueous mixture of Sodium dodecyl sulfate and 1-dodecanol: Using a 500 mL volumetric flask, sodium dodecyl sulfate or SDS (7.2 g) was added along with 1-dodecanol (0.2 g). Enough deionized water was added to make a 500 mL solution of SDS/1-Dodecanol with concentrations [SDS]=0.02 M and [1-Dodecanol]=0.0022 M. The mixture was stirred at 50° C. until all the solutes completely dissolved, which usually takes several hours (8 hours) of gentle stirring. The homogenous solution was filtered while warm through a 0.2 micron nitrocellulose filter to remove dust and particulates. The solution was stored in a clean glass bottle. When the solution cooled below 25° C., a precipitate of 1-dodecanol separates out. Warming the mixture above 25° C. re-dissolves the aliphatic alcohol.

Preparation of the light-responsive microwires: To a clean glass vial (50 mL capacity) 40 mL of the SDS/1-Dodecanol solution was added. The solution was warmed to 55° C. A 20 solution of cis-9DVAM in N,N-DMF was prepared by dissolving 2 mg in 50 μL of DMF. The cis-9DVAM solution in DMF was rapidly injected with a gentle swirl in the pre-heated surfactant solution. This formed an orange, translucent solution that was incubated in an oven set at 47° C. for 48 hours without agitation. After 48 hours, ultralong and thin microwires made from cis-9DVAM were observed suspended in solution. Roughly half of the injected cis-9DVAM remains in solution while the other half separate as microwires. FIG. 13 shows a 50 mL capacity bottle of the solution after 48 hours of incubation at 47° C., where the formation of the microwires appear as red hair-like fibers suspended mid solution. The suspension was suction filtered over a cellulose filter paper and then resuspended in 2 mL of a 0.02 M SDS solution without 1-dodecanol. FIG. 14 shows an image of the filter paper with the microwires. FIGS. 15A-D shows SEM images of the microwires deposited over conductive carbon tape and coated with a thin layer of Pt. FIGS. 15A, 15B, 15C, 15D are at magnifications of ×30, ×200, ×500, and ×1400, respectively.

Observing Light-Induced Motion of the Microwires:

A drop (50 μL) of the microwire suspension in SDS solution was deposited over a microscope glass slide. A 1 cm×1 cm microscope coverslip was placed on top of the drop. The glass slide was placed on an OPTIKA fluorescence microscope sample stage. Light from the halogen lamp with an intensity of 140 Klux was filtered through a 590 nm long-pass filter. At the same time, UV light from a 365 nm bandpass filter irradiated the sample. Gentle attenuation of the visible light (increasing or decreasing intensity) initiated autonomous motion of the microwires. An example of the microscope setup used is shown in FIG. 16

As indicated in the above, molecular crystal microwires made from cis-2-(3-anthracen-9-yl-allylidene)-malononitrile were synthesized using the co-precipitation technique from an aqueous mixture of sodium dodecyl sulfate/1-dodecanol. Microwires with an average length of 2,500 μm and an average thickness of 7 μm separated out of the solution after incubation at 47° C. for a period of 48 hours. These highly crystalline microwires absorb visible and UV light and transform the absorbed light energy into motion in the form of autonomous wiggling, bending, or rotation around the long axis. The intensity of wiggling motion is a function of the intensity, direction, and wavelength of light used.

The invention claimed is:

1. A method of exfoliating a microcrystal of cis-dimethyl-2(3-(anthracen-9-yl)allylidene)malonate, the method comprising:
    irradiating a microcrystal of cis-dimethyl-2(3-(anthracen-9-yl)allylidene)malonate with light having a wavelength of 250-410 nm,
    wherein the irritating induces in a portion of the microcrystal a cis-trans isomerization of cis-dimethyl-2(3-(anthracen-9-yl)allylidene)malonate to trans-dimethyl-2(3-(anthracen-9-yl)allylidene)malonate,
    wherein the irradiating separates an outer layer from the microcrystal to produce an exfoliated microcrystal, the outer layer having a thickness of 200-600 nm, and
    irradiating the exfoliated microcrystal with light having a wavelength of 250-410 nm to produce a second exfoliated microcrystal and a second layer having a thickness of 200-600 nm.

2. The method of claim 1, wherein the microcrystal comprises at least 70 wt % cis-dimethyl-2(3-(anthracen-9-yl)allylidene)malonate in crystalline form, relative to a total weight of the microcrystal.

3. The method of claim 2, wherein the microcrystal comprises at least 80 wt % cis-dimethyl-2(3-(anthracen-9-yl)allylidene)malonate in crystalline form, relative to a total weight of the microcrystal.

4. The method of claim 1, wherein the microcrystal is irradiated for an exposure time of 0.4-2.0 s.

5. The method of claim 4, wherein the microcrystal is irradiated with light having a light power density of 1-200 mW/cm$^2$.

6. The method of claim 1, wherein the light is from a continuous or pulsed laser.

7. The method of claim 1, wherein the light is from a mercury or xenon gas discharge lamp.

8. The method of claim 1, wherein the microcrystal is a component of an adhesive.

9. The method of claim 1, wherein the microcrystal is a component of an implant or orthopedic device.

10. The method of claim 1, wherein the microcrystal is a component of a photosensitive switch.

11. The method of claim 1, wherein the microcrystal is a component of a composition that comprises a dye or a pigment.

12. A method of exfoliating a microcrystal, the method comprising:

irradiating a microcrystal of cis-dimethyl-2(3-(anthracen-9-yl)allylidene)malonate with light having a wavelength of 220-420 nm,
  wherein the microcrystal is in the form of a rectangular block having a longest linear dimension of 5-100 μm and an aspect ratio of 1:1-10:1,
  wherein the microcrystal is formed by seeding a solution of dissolved cis-dimethyl-2(3-(anthracen-9-yl)allylidene)malonate with a crystal of cis-dimethyl-2(3-(anthracen-9-yl)allylidene)malonate, wherein the crystal has an octahedral form,
  wherein the irradiating induces in a portion of the microcrystal a cis-trans isomerization of cis-dimethyl-2(3-(anthracen-9-yl)allylidene)malonate to trans-dimethyl-2(3-(anthracen-9-yl)allylidene)malonate, and
  wherein the irradiating separates an outer layer from the microcrystal to produce an exfoliated microcrystal, the outer layer having a thickness of 350-450 nm.

13. The method of claim 12, wherein the microcrystal is in the form of a square cuboid.

14. The method of claim 12, wherein the microcrystal is dispersed within a second solution comprising a surfactant.

15. The method of claim 12, wherein the microcrystal of cis-dimethyl-2(3-(anthracen-9-yl)allylidene)malonate is produced by irradiating a compound of trans-dimethyl-2(3-(anthracen-9-yl)allylidene)malonate with light having a visible wavelength.

16. The method of claim 12, wherein the microcrystal is irradiated for an exposure time of 0.5-1.8 s.

17. The method of claim 16, wherein the microcrystal is irradiated with light having a light power density of 40-110 mW/cm$^2$.

18. The method of claim 12, wherein the microcrystal is in the form of a rectangular block having a longest linear dimension of 6-25 μm.

* * * * *